US010406056B2

(12) United States Patent  (10) Patent No.: US 10,406,056 B2
Courtine et al.  (45) Date of Patent: Sep. 10, 2019

(54) APPARATUS AND METHOD FOR RESTORING VOLUNTARY CONTROL OF LOCOMOTION IN NEUROMOTOR IMPAIRMENTS

(71) Applicant: ECOLE POLYTECHNIQUE FEDERALE DE LAUSANNE (EPFL), Lausanne (CH)

(72) Inventors: Grégoire Courtine, Lausanne (CH); Silvestro Micera, Genève (CH); Joachim Von Zitzewitz, Lausanne (CH)

(73) Assignee: Ecole Polytechnique Federale De Lausanne (EPFL), Lausanne (CH)

( * ) Notice: Subject to any disclaimer, the term of this patent is extended or adjusted under 35 U.S.C. 154(b) by 0 days.

(21) Appl. No.: 15/667,843

(22) Filed: Aug. 3, 2017

(65) Prior Publication Data
US 2017/0325719 A1  Nov. 16, 2017

Related U.S. Application Data

(62) Division of application No. 14/404,853, filed as application No. PCT/IB2013/054421 on May 29, 2013, now Pat. No. 9,968,406.
(Continued)

(51) Int. Cl.
*A61B 5/00* (2006.01)
*A61H 1/02* (2006.01)
(Continued)

(52) U.S. Cl.
CPC ......... *A61H 1/0262* (2013.01); *A61B 5/0004* (2013.01); *A61B 5/0048* (2013.01);
(Continued)

(58) Field of Classification Search
CPC ..... A61B 5/112; A61B 5/0004; A61B 5/0048; A61B 5/0053; A61B 5/04001; A61B 5/0482
See application file for complete search history.

(56) References Cited

U.S. PATENT DOCUMENTS 5,002,053 A  3/1991  Garcia-Rill et al.
6,080,087 A  6/2000  Bingham
(Continued)

FOREIGN PATENT DOCUMENTS

CN  101822223 A  9/2010
JP  2009512516 A  3/2009
(Continued)

OTHER PUBLICATIONS

Guyatt, G. et al., "The 6-minute walk: a new measure of exercise capacity in patients with chronic heart failure," Canadian Medical Association Journal, vol. 132, No. 8, Apr. 15, 1985, 5 pages.
(Continued)

*Primary Examiner* — Amanda K Hulbert
*Assistant Examiner* — Natasha Patel
(74) *Attorney, Agent, or Firm* — McCoy Russell LLP

(57) ABSTRACT

It is disclosed an apparatus for restoring voluntary control of locomotion in a subject suffering from a neuromotor impairment comprising a multidirectional trunk support system and a device for epidural electrical stimulation. The robotic interface is capable of evaluating, enabling and training motor pattern generation and balance across a variety of natural walking behaviors in subjects with neuromotor impairments. Optionally, pharmacological cocktails can be administered to enhance rehabilitation results. It is also disclosed a method for the evaluation, enablement and training of a subject suffering from neuromotor impairments by combining robotically assisted evaluation tools with
(Continued)

Figure 1:
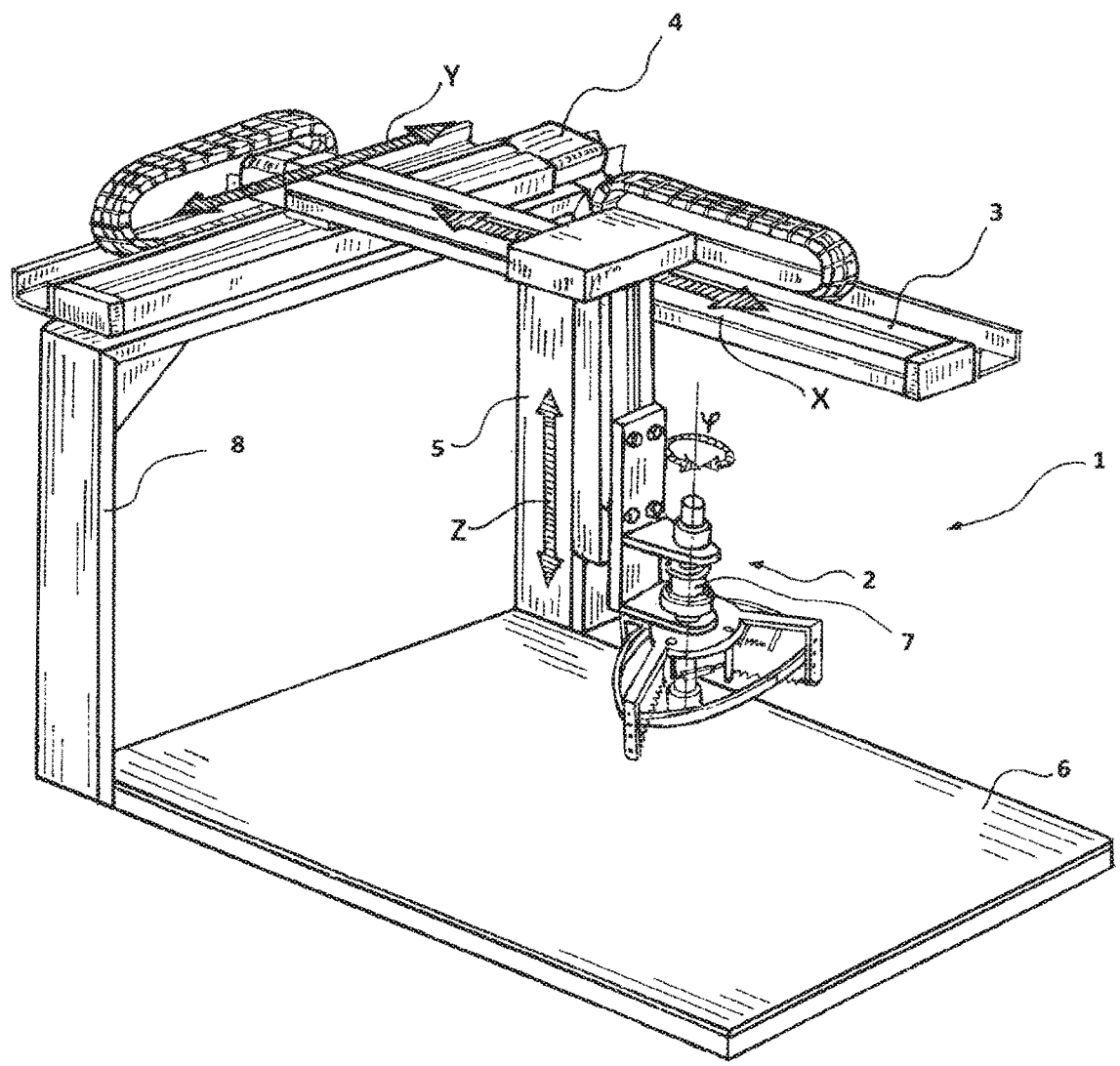

sophisticated neurobiomechanical and statistical analyzes. A method for the rehabilitation (by this term also comprising restoring voluntary control of locomotion) of a subject suffering from a neuromotor impairment in particular partial or total paralysis of limbs, is also disclosed.

9 Claims, 5 Drawing Sheets

Related U.S. Application Data

(60) Provisional application No. 61/653,021, filed on May 30, 2012.

(51) Int. Cl.

| | |
|---|---|
| *A61N 1/36* | (2006.01) |
| *B25J 9/00* | (2006.01) |
| *A63B 69/00* | (2006.01) |
| *A63B 24/00* | (2006.01) |
| *A63B 21/00* | (2006.01) |
| *A61B 5/11* | (2006.01) |
| *A61K 31/135* | (2006.01) |
| *A61K 31/496* | (2006.01) |
| *A61K 31/55* | (2006.01) |
| *A61B 34/30* | (2016.01) |
| *A61H 1/00* | (2006.01) |
| *A61B 5/04* | (2006.01) |
| *A61B 5/0482* | (2006.01) |
| *A61B 5/0484* | (2006.01) |
| *A61B 5/103* | (2006.01) |
| *A63B 22/02* | (2006.01) |
| *A63B 22/20* | (2006.01) |
| *A63B 22/00* | (2006.01) |

(52) U.S. Cl.
CPC .......... *A61B 5/0053* (2013.01); *A61B 5/0057* (2013.01); *A61B 5/04001* (2013.01); *A61B 5/0482* (2013.01); *A61B 5/0484* (2013.01); *A61B 5/112* (2013.01); *A61B 5/1123* (2013.01); *A61B 5/1124* (2013.01); *A61B 5/4005* (2013.01); *A61B 5/4023* (2013.01); *A61B 5/4076* (2013.01); *A61B 5/4519* (2013.01); *A61B 5/4538* (2013.01); *A61B 5/4566* (2013.01); *A61B 5/4824* (2013.01); *A61B 5/4848* (2013.01); *A61B 5/70* (2013.01); *A61B 5/721* (2013.01); *A61B 34/30* (2016.02); *A61H 1/001* (2013.01); *A61H 1/0229* (2013.01); *A61K 31/135* (2013.01); *A61K 31/496* (2013.01); *A61K 31/55* (2013.01); *A61N 1/36003* (2013.01); *A63B 21/00181* (2013.01); *A63B 24/0087* (2013.01); *A63B 69/0057* (2013.01); *A63B 69/0064* (2013.01); *B25J 9/0006* (2013.01); *A61B 5/1036* (2013.01); *A61B 2034/302* (2016.02); *A61B 2560/02* (2013.01); *A61H 2201/0196* (2013.01); *A61H 2201/165* (2013.01); *A61H 2201/1666* (2013.01); *A61H 2201/5007* (2013.01); *A61H 2201/5061* (2013.01); *A61H 2201/5069* (2013.01); *A61H 2230/08* (2013.01); *A61H 2230/085* (2013.01); *A61N 1/36057* (2013.01); *A63B 22/0235* (2013.01); *A63B 22/203* (2013.01); *A63B 2022/0094* (2013.01); *A63B 2022/206* (2013.01); *A63B 2213/004* (2013.01); *A63B 2220/10* (2013.01); *A63B 2220/51* (2013.01)

(56) References Cited

U.S. PATENT DOCUMENTS

| | | |
|---|---|---|
| 6,666,831 B1 | 12/2003 | Edgerton et al. |
| 7,125,388 B1 | 10/2006 | Reinkensmeyer et al. |
| 2003/0139422 A1 | 7/2003 | Teng |
| 2007/0004567 A1 | 1/2007 | Shetty et al. |
| 2007/0179534 A1* | 8/2007 | Firlik ................ A61B 5/16 607/3 |
| 2007/0250119 A1 | 10/2007 | Tyler et al. |
| 2009/0227925 A1* | 9/2009 | McBean ............ A61F 5/0127 602/16 |
| 2010/0016732 A1 | 1/2010 | Wells et al. |
| 2010/0324699 A1 | 12/2010 | Herr et al. |

FOREIGN PATENT DOCUMENTS

| | | |
|---|---|---|
| JP | 2011504112 A | 2/2011 |
| WO | 2007047852 A2 | 4/2007 |

OTHER PUBLICATIONS

Lovely, R. et al., "Effects of Training on the Recovery of Full-Weight-Bearing Stepping in the Adult Spinal Cat," Experimental Neurology, vol. 92, No. 2, May 1986, 15 pages.
Barbeau, H. et al., "Recovery of locomotion after chronic spinalization in the adult cat," Brain Research, vol. 412, No. 1, May 26, 1987, 12 pages.
Colgate, E. et al., "An Analysis of Contact Instability in Terms of Passive Physical Equivalents," Proceedings of the 1989 IEEE International Conference on Robotics and Automation, May 14, 1989, Scottsdale, Arizona, 6 pages.
Wernig, A. et al., "Laufband locomotion with body weight support improved walking in persons with severe spinal cord injuries," Paraplegia, vol. 30, No. 4, Apr. 1992, 10 pages.
Winter, D. et al., "An integrated EMG/biomechanical model of upper body balance and posture during human gait," Progress in Brain Research, vol. 97, Chapter 32, Available as Early as Jan. 1, 1993, 9 pages.
Wernig, A. et al., "Laufband Therapy Based on 'Rules of Spinal Locomotion' is Effective in Spinal Cord Injured Persons," European Journal of Neuroscience, vol. 7, No. 4, Apr. 1995, 7 pages.
Pratt, G. et al., "Stiffness Isn't Everything," Proceedings of the Fourth International Symposium on Experimental Robotics (ISER '95), Jun. 30, 1995, Stanford, California, 6 pages.
Basso, D. et al., "MASCIS Evaluation of Open Field Locomotor Scores: Effects of Experience and Teamwork on Reliability," Journal of Neurotrauma, vol. 13, No. 7, Jul. 1996, 17 pages.
Harkema, S. et al., "Human Lumbosacral Spinal Cord Interprets Loading During Stepping," Journal of Neurophysiology, vol. 77, No. 2, Feb. 1, 1997, 15 pages.
Brosamle, C. et al., "Cells of Origin, Course, and Termination Patterns of the Ventral, Uncrossed Component of the Mature Rat Corticospinal Tract," The Journal of Comparative Neurology, vol. 386, No. 2, Sep. 22, 1997, 11 pages.
Kakulas, B., "A Review of the Neuropathology of Human Spinal Cord Injury with Emphasis on Special Features," Proceedings of the Donald Munro Memorial Lecture at the American Paraplegia Society 44th Annual Conference, Sep. 9, 1998, Las Vegas, Nevada, 6 pages.
Hashtrudi-Zaad, K. et al., "On the Use of Local Force Feedback for Transparent Teleoperation," Proceedings of the 1999 IEEE International Conference on Robotics and Automation, May 10, 1999, Detroit, Michigan, 7 pages.
Kirkwood, P., "Neuronal Control of Locomotion: From Mollusc to Man—G.N. Orlovsky, T.G. Deliagina and S. Grillner. Oxford University Press, Oxford, 1999. ISBN 0198524056 (Hbk), 322 pp.," Clinical Neurophysiology, vol. 111, No. 8, Aug. 1, 2000, Published Online Jul. 17, 2000, 2 pages.
Pratt, J. et al., "Series elastic actuators for high fidelity force control," Industrial Robot: An International Journal, vol. 29, No. 3, Available as Early as Jan. 1, 2002, 13 pages.

(56) References Cited

OTHER PUBLICATIONS

Steward, O. et al. "False Resurrections: Distinguishing Regenerated from Spared Axons in the Injured Central Nervous System," The Journal of Comparative Neurology, vol. 459, No. 1, Apr. 21, 2003, 8 pages.
Pearson, K., "Generating the walking gait: role of sensory feedback," Progress in Brain Research, vol. 143, Chapter 12, Published Online Nov. 28, 2003, 7 pages.
Bareyre, F. et al., "The injured spinal cord spontaneously forms a new intraspinal circuit in adult rats," Nature Neuroscience, vol. 7, No. 3, Mar. 2004, Published Online Feb. 15, 2004, 9 pages.
Liu, J. et al., "Stimulation of the Parapyramidal Region of the Neonatal Rat Brain Stem Produces Locomotor-Like Activity Involving Spinal 5-HT7 and 5-HT2A Receptors," Journal of Neurophysiology, vol. 94, No. 2, Aug. 1, 2005, Published Online May 4, 2005, 13 pages.
Timoszyk, W. et al., "Hindlimb loading determines stepping quantity and quality following spinal cord transection," Brain Research, vol. 1050, No. 1-2, Jul. 19, 2005, Published Online Jun. 24, 2005, 10 pages.
Wernig, A., "Ineffectiveness' of Automated Locomotor Training," Archives of Physical Medicine and Rehabilitation, vol. 86, No. 12, Dec. 2005, 2 pages.
Nessler, J. et al., "A Robotic Device for Studying Rodent Locomotion After Spinal Cord Injury," IEEE Transactions on Neural Systems and Rehabilitation Engineering, vol. 13, No. 4, Dec. 12, 2005, 10 pages.
Reinkensmeyer, D. et al., "Tools for understanding and optimizing robotic gait training," Journal of Rehabilitation Research & Development, vol. 43, No. 5, Aug. 2006, 14 pages.
Frey, M. et al., "A Novel Mechatronic Body Weight Support System," IEEE Transactions on Neural Systems and Rehabilitation Engineering, vol. 14, No. 3, Sep. 18, 2006, 11 pages.
Cai, L. et al., "Implications of Assist-As-Needed Robotic Step Training after a Complete Spinal Cord Injury on Intrinsic Strategies of Motor Learning," The Journal of Neuroscience, vol. 26, No. 41, Oct. 11, 2006, 5 pages.
Courtine, G. et al., "Can experiments in nonhuman primates expedite the translation of treatments for spinal cord njury in humans?," Nature Medicine, vol. 13, No. 5, May 2007, 13 pages.
Drew, T. et al., "Cortical mechanisms involved in visuomotor coordination during precision walking," Brain Research Reviews, vol. 57, No. 1, Jan. 2008, Published Online Aug. 22, 2007, 13 pages.
Edgerton, V. et al., "Training Locomotor Networks," Brain Research Reviews, vol. 57, No. 1, Jan. 2008, Published Online Sep. 16, 2007, 25 pages.
Kwakkel, G. et al., "Effects of Robot-assisted therapy on upper limb recovery after stroke: A Systematic Review," Neruorehabilitation and Neural Repair, vol. 22, No. 2, Mar. 2008, Published Online Sep. 17, 2007, 17 pages.
Cowley, K. et al., "Propriospinal neurons are sufficient for bulbospinal transmission of the locomotor command signal in the neonatal rat spinal cord," The Journal of Physiology, vol. 586, No. 6, Mar. 15, 2008, Published Online Jan. 31, 2008, 13 pages.
Vallery, H. et al., "Compliant Actuation of Rehabilitation Robots," IEEE Robotics & Automation Magazine, vol. 15, No. 3, Sep. 12, 2008, 10 pages.
Edgerton, V. et al., "Robotic Training and Spinal Cord Plasticity," Brain Research Bulletin, vol. 78, No. 1, Jan. 15, 2009, Published Online Nov. 14, 2008, 19 pages.
Alto, L. et al., "Chemotropic Guidance Facilitates Axonal Regeneration and Synapse Formation after Spinal Cord Injury," Nature Neuroscience, vol. 12, No. 9, Sep. 2009, Published Online Aug. 2, 2009, 22 pages.
Hagglund, M. et al., "Activation of groups of excitatory neurons in the mammalian spinal cord or hindbrain evokes locomotion," Nature Neuroscience, vol. 13, No. 2, Feb. 2010, Published Online Jan. 17, 2010, 8 pages.
Wessels, M. et al., "Body Weight-Supported Gait Training for Restoration of Walking in People With an Incomplete Spinal Cord Injury: A Systematic Review," Journal of Rehabilitation Medicine, vol. 42, No. 6, Jun. 2010, 7 pages.
Zorner, B. et al., "Profiling locomotor recovery: comprehensive quantification of impairments after CNS damage in rodents," Nature Methods, vol. 7, No. 9, Sep. 2010, Published Online Aug. 15, 2010, 11 pages.
Ada, L. et al., "Mechanically assisted walking with body weight support results in more independent walking than assisted overground walking in non-ambulatory patients early after stroke: a systematic review," Journal of Physiotherapy, vol. 56, No. 3, Sep. 2010, 9 pages.
Duschau-Wicke, A. et al., "Patient-cooperative control increases active participation of individuals with SCI during robot-aided gait training," Journal of NeuroEngineering and Rehabilitation, vol. 7, No. 43, Sep. 10, 2010, 13 pages.
Rosenzweig, E. et al., "Extensive Spontaneous Plasticity of Corticospinal Projections After Primate Spinal Cord Injury," Nature Neuroscience, vol. 13, No. 12, Dec. 2010, Published Online Nov. 14, 2010, 19 pages.
Hidler, J. et al., "ZeroG: Overground gait and balance training system," Journal of Rehabilitation Research & Development, vol. 48, No. 4, Available as Early as Jan. 1, 2011, 12 pages.
Musselman, K. et al., "Spinal Cord Injury Functional Ambulation Profile: A New Measure of Walking Ability," Neurorehabilitation and Neural Repair, vol. 25, No. 3, Mar. 2011, Published Online Feb. 25, 2011, 9 pages.
Wirz, M. et al., "Effectiveness of automated locomotor training in patients with acute incomplete spinal cord injury: A randomized controlled multicenter trial," BMC Neurology, vol. 11, No. 60, May 27, 2011, 5 pages.
Sun, F. et al., "Sustained axon regeneration induced by co-deletion of PTEN and SOCS3," Nature, vol. 480, No. 7377, Dec. 15, 2011, Published Online Nov. 6, 2011, 12 pages.
Carhart, M. et al., "Epidural Spinal-Cord Stimulation Facilitates Recovery of Functional Walking Following Incomplete Spinal-Cord Injury," IEEE Transactions on Neural Systems and Rehabilitation Engineering, vol. 12, No. 1, Mar. 15, 2004, 11 pages.
Courtine, G. et al., "Recovery of supraspinal control of stepping via indirect propriospinal relay connections after spinal cord injury," Nature Medicine, vol. 14, No. 1, Published Online Jan. 6, 2008, 6 pages.
Fuentes, R. et al., "Spinal Cord Stimulation Restores Locomotion in Animal Models of Parkinson's Disease," Science Magazine, vol. 323, No. 5921, Mar. 20, 2009, 5 pages.
Musienko, P. et al., "Combinatory Electrical and Pharmacological Neuroprosthetic Interfaces to Regain Motor Function After Spinal Cord Injury," IEEE Transactions on Biomedical Engineering, vol. 56, No. 11, Nov. 2009, Published Online Jul. 24, 2009, 5 pages.
Courtine, G. et al., "Transformation of nonfunctional spinal circuits into functional states after the of brain input," Nature Neuroscience, vol. 12, No. 10, Oct. 2009, Published Online Sep. 20, 2009, 12 pages.
Harkema, S. et al., "Effect of epidural stimulation of the lumbosacral spinal cord on voluntary movement, standing, and assisted stepping after motor complete paraplegia: a case study," The Lancet, vol. 377, No. 9781, May 20, 2011, 12 pages.
Musienko, P. et al., "Controlling Specific Locomotor Behaviors through Multidimensional Monoaminergic Modulation of Spinal Circuitries," Journal of Neuroscience, vol. 31, No. 25, Jun. 22, 2011, 15 pages.
Musienko, P. et al., "Multi-system neurorehabilitative strategies to restore motor functions following severe spinal cord injury," Experimental Neurology, vol. 235, No. 1, May 2012, Published Online Sep. 7, 2011, 10 pages.
Courtine, G. et al., "Apparatus and Method for Restoring Voluntary Control of Locomotion in Neuromotor Impairments," U.S. Appl. No. 15/667,816, filed Aug. 3, 2017, 58 pages.
Japanese Patent Office, Office Action Issued in Application No. 2015514657, dated Jan. 9, 2018, 12 pages. (Submitted with Machine Translation).

(56) References Cited

OTHER PUBLICATIONS

United States Patent and Trademark Office, Office Action Issued in U.S. Appl. No. 15/667,816, dated Mar. 20, 2018, 21 pages.

* cited by examiner

APPARATUS AND METHOD FOR RESTORING VOLUNTARY CONTROL OF LOCOMOTION IN NEUROMOTOR IMPAIRMENTS

CROSS-REFERENCE TO RELATED APPLICATIONS

The present application is a divisional application of U.S. patent application Ser. No. 14/404,853, entitled "APPARATUS AND METHOD FOR RESTORING VOLUNTARY CONTROL OF LOCOMOTION IN NEUROMOTOR IMPAIRMENTS," filed on Dec. 1, 2014. U.S. patent application Ser. No. 14/404,853 is the U.S. national phase of International Application No. PCT/IB2013/054421, entitled "APPARATUS AND METHOD FOR RESTORING VOLUNTARY CONTROL OF LOCOMOTION IN NEUROMOTOR IMPAIRMENTS," filed on May 29, 2013. International Application No. PCT/IB2013/054421 claims priority to U.S. Provisional Patent Application No. 61/653,021, filed on May 30, 2012. The entire contents of each of the above-identified applications are hereby incorporated by reference in their entirety for all purposes.

TECHNICAL FIELD

The present invention relates to the field of medical engineering, in particular to devices and systems for rehabilitation of injured subjects, more in particular for the rehabilitation of the locomotion system, especially limbs.

BACKGROUND OF THE INVENTION

Neuromotor disorders such as spinal cord injury (SCI) and stroke lead to distinct impairments of motor pattern generation and balance (Courtine, G., et al. Transformation of nonfunctional spinal circuits into functional states after the loss of brain input. *Nat Neurosci* 12, 1333-1342 (2009); Harkema, S. J., et al. Human lumbosacral spinal cord interprets loading during stepping. *J Neurophysiol* 77, 797-811 (1997).)

Consequently, dissociating these sub-functions is essential for assessment and neurorehabilitation of gait. Conceptually, neurorehabilitation systems should act as a propulsive or postural neuroprosthesis that assist or perturb propulsion, balance, or the combination of both to varying degrees according to experimental purposes or patient-specific needs.

Existing systems used to compensate for impaired propulsion and balance rely on passive spring support, counterweight mechanisms, or closed-loop force control systems that generate vertical forces at the trunk level during treadmill-restricted stepping (Nessler, J. A., et al. A robotic device for studying rodent locomotion after spinal cord injury. *IEEE transactions on neural systems and rehabilitation engineering: a publication of the IEEE Engineering in Medicine and Biology Society* 13, 497-506 (2005); Frey, M., et al. A novel mechatronic body weight support system. *IEEE transactions on neural systems and rehabilitation engineering: a publication of the IEEE Engineering in Medicine and Biology Society* 14, 311-321 (2006)). However, these approaches present several drawbacks: (i) current systems only provide support in the vertical direction whereas well-balanced locomotion requires finely tuned trunk movements in virtually every direction (Winter, D. A., MacKinnon, C. D., Ruder, G. K. & Wieman, C. An integrated EMG/biomechanical model of upper body balance and posture during human gait. *Prog Brain Res* 97, 359-367 (1993)); (ii) the optic flow, which significantly modulates locomotion (Orlovsky, G. N., Deliagina, T. G. & Grillner, S. *Neuronal control of locomotion: from mollusc to man*, (Oxford University Press, Oxford, 1999)), is suppressed during treadmill-restricted stepping; (iii) rehabilitation is restricted to stepping on a treadmill (Musselman, K., Brunton, K., Lam, T. & Yang, J. Spinal cord injury functional ambulation profile: a new measure of walking ability. *Neuro rehabilitation and neural repair* 25, 285-293 (2011)); a condition that markedly differs from the rich repertoire of natural locomotor tasks.

Robotic systems have been designed to overcome these limitations. The ZeroG (Hidler, J., et al. ZeroG: overground gait and balance training system. *Journal of rehabilitation research and development* 48, 287-298 (2011)) provides vertical support during overground walking using a lifting unit mounted on a rail-guided trolley. However, the rails constrain subjects along a fixed direction, and trunk support is restricted to the vertical direction. The NaviGaitor (Shetty, D., Fast, A. & Campana, C. A. Ambulatory suspension and rehabilitation apparatus (U.S. Pat. No. 7,462,138)) allows translations in all directions by means of an overhead linear multi-axis system, but its massive structure leads to high inertia that prevents normal-paced movements.

Therefore, there is the problem to have a robotic system which overcomes the drawbacks of the prior art. In particular, there is the need of a multidirectional trunk support system that solves these various issues.

Another problem in the art is that the evaluation of locomotor function in subjects often relies on visual scoring systems (Basso, D. M., et al. MASCIS evaluation of open field locomotor scores: effects of experience and teamwork on reliability. Multicenter Animal Spinal Cord Injury Study. *Journal of neurotrauma* 13, 343-359 (1996)) or single-variable analysis (Zörner, B., et al. Profiling locomotor recovery: comprehensive quantification of impairments after CNS damage in rodents. *Nature methods* 7, 701-708 (2010)) that not only lack objectivity but also fail to capture the multidimensional correlative structures of locomotor control strategies (Musienko, P., et al. Controlling specific locomotor behaviors through multidimensional monoaminergic modulation of spinal circuitries. *J Neurosci* 31, 9264-9278 (2011)).

It is well-known that activity-based interventions exploiting proprioceptive information to enhance spinal motor output during training (H. Barbeau, S. Rossignol, Recovery of locomotion after chronic spinalization in the adult cat. *Brain Res* 412, 84 (May 26, 1987); R. G. Lovely, R. J. Gregor, R. R. Roy, V. R. Edgerton, Effects of training on the recovery of full-weight-bearing stepping in the adult spinal cat. *Experimental neurology* 92, 421 (May, 1986); A. Wernig, S. Muller, Laufband locomotion with body weight support improved walking in persons with severe spinal cord injuries. *Paraplegia* 30, 229 (April, 1992)) promote plastic changes capable of restoring locomotion after severe though incomplete spinal cord injury (SCI) (A. Wernig, S. Muller, Laufband locomotion with body weight support improved walking in persons with severe spinal cord injuries. *Paraplegia* 30, 229 (April, 1992); A. Wernig, S. Muller, A. Nanassy, E. Cagol, Laufband therapy based on 'rules of spinal locomotion' is effective in spinal cord injured persons. *Eur J Neurosci* 7, 823 (Apr. 1, 1995)).

A recent case study suggests that, in combination with epidural electrical stimulation of lumbosacral segments, activity-based rehabilitation may also restore supraspinally-mediated movements after motor complete paraplegia (Harkema, S., et al. Effect of epidural stimulation of the lumbosacral spinal cord on voluntary movement, standing, and assisted stepping after motor complete paraplegia: a case study *Lancet*, 377, 1938 (Jun. 4, 2011)).

There is a mosaic of evidence suggesting that gait rehabilitation should be conducted overground (Wessels, M., Lucas, C., Eriks, I. & de Groot, S. Body weight-supported gait training for restoration of walking in people with an incomplete spinal cord injury: a systematic review. *Journal of rehabilitation medicine: official journal of the UEMS European Board of Physical and Rehabilitation Medicine* 42, 513-519 (2010)), across multiple walking paradigms (Musselman, K., Brunton, K., Lam, T. & Yang, J. Spinal cord injury functional ambulation profile: a new measure of walking ability. *Neurorehabilitation and neural repair* 25, 285-293 (2011)), with adequate support conditions (Wessels, M., Lucas, C., Eriks, I. & de Groot, S. Body weight-supported gait training for restoration of walking in people with an incomplete spinal cord injury: a systematic review. *Journal of rehabilitation medicine: official journal of the UEMS European Board of Physical and Rehabilitation Medicine* 42, 513-519 (2010); Reinkensmeyer, D. J., et al. Tools for understanding and optimizing robotic gait training. *Journal of rehabilitation research and development* 43, 657-670 (2006); Ada, L., Dean, C. M., Vargas, J. & Ennis, S. Mechanically assisted walking with body weight support results in more independent walking than assisted overground walking in non-ambulatory patients early after stroke: a systematic review. *Journal of physiotherapy* 56, 153-161 (2010)), enabling systems (Courtine, G., et al. Transformation of nonfunctional spinal circuits into functional states after the loss of brain input. *Nat Neurosci* 12, 1333-1342 (2009); Harkema, S., et al. Effect of epidural stimulation of the lumbosacral spinal cord on voluntary movement, standing, and assisted stepping after motor complete paraplegia: a case study. *Lancet* 377, 1938-1947 (2011); Kwakkel, G., Kollen, B. J. & Krebs, H. I. Effects of robot-assisted therapy on upper limb recovery after stroke: a systematic review. *Neurorehabilitation and neural repair* 22, 111-121 (2008); Edgerton, V. R. & Roy, R. R. Robotic training and spinal cord plasticity. *Brain research bulletin* 78, 4-12 (2009); Reinkensmeyer, D. J., et al. Tools for understanding and optimizing robotic gait training. *Journal of rehabilitation research and development* 43, 657-670 (2006)), task-specific sensory cues (Courtine, G., et al. Transformation of nonfunctional spinal circuits into functional states after the loss of brain input. *Nat Neurosci* 12, 1333-1342 (2009); Harkema, S., et al. Effect of epidural stimulation of the lumbosacral spinal cord on voluntary movement, standing, and assisted stepping after motor complete paraplegia: a case study. *Lancet* 377, 1938-1947 (2011)), and active patient cooperation (Duschau-Wicke, A., Caprez, A. & Riener, R. Patient-cooperative control increases active participation of individuals with SCI during robot-aided gait training. *Journal of neuroengineering and rehabilitation* 7, 43 (2010); Edgerton, V. R. & Roy, R. R. Robotic training and spinal cord plasticity. *Brain research bulletin* 78, 4-12 (2009)), but these concepts remain fragmented and there is no indication on how to arrive at a unified therapeutic tool to evaluate and restore locomotor function after CNS disorders, both in animals and in humans.

Moreover, according to the state of the art, voluntary control of movement still cannot be achieved by the subject.

There is still the problem to provide a method for rehabilitation of a subject suffering from neuromuscular disturbance, in particular partial or total paralysis of limbs, this method achieving voluntary control of movement.

There is also the need to provide an apparatus for restoring voluntary control of locomotion in a neuromotor impairment which is capable of acting as a propulsive or postural neuroprosthesis that assists or perturbs propulsion, balance, or the combination of both to varying degrees according to experimental purposes or patient-specific needs. In particular, this apparatus should be capable of performing an objective evaluation of locomotor functions, capturing the multidimensional correlative structures of locomotion functions. Further, such an apparatus should be able to guide the subject in need of restoring voluntary control of locomotion and also to be "transparent" to the subject, as the case may be.

SUMMARY OF THE INVENTION

It has now been found that combining a multidirectional trunk support system with a device for epidural electrical stimulation solves the problems of the prior art.

Therefore, it is an object of the present invention an apparatus for restoring voluntary control of locomotion in a subject suffering from a neuromotor impairment comprising a multidirectional trunk support system and a device for epidural electrical stimulation, as defined in the appended claims.

It is another object of the present invention, a robotic interface capable of evaluating, enabling and training motor pattern generation and balance across a variety of natural walking behaviors in subjects with neuromotor impairments, as defined in the appended claims. Surprisingly, providing this robotic interface with a device for epidural electric stimulation, optionally with pharmacological cocktails, together with some improvements in the robotic interface, results in an apparatus for restoring voluntary control of locomotion in a subject suffering from a neuromotor impairment capable of achieving rehabilitation results far higher than the apparatuses of the prior art.

It has also been found, and is another object of the present invention, a method for the evaluation, enablement and training of a subject suffering from neuromotor impairments, as defined in the appended claims, by combining robotically assisted evaluation tools with sophisticated neurobiomechanical and statistical analyses. Said method provides the means for assessing the control of, and interactions between, gait and balance with refinement and objectivity.

It has further been found, and is an object of the present invention, a method for the rehabilitation (by this term also comprising restoring voluntary control of locomotion) of a subject suffering from a neuromotor impairment in particular partial or total paralysis of limbs, this method achieving voluntary control of movement, comprising applying electrical and optionally pharmacological stimulation and using the above robotic interface in an overground training programme.

In an embodiment of the present invention, in said apparatus, said multidirectional trunk support system provides support to said subject against gravity.

In another embodiment of the present invention, said multidirectional trunk support system comprises:
a. a robotic interface having end effectors with n actuated degrees of freedom;
b. means integrated in or attached to said robotic interface to provide compliant/elastic or viscoelastic behavior at said robot's end effectors in said degrees of freedom;

c. sensors to measure the movement of said end effectors resulting exclusively from this compliance; or sensors to measure the force (wrench) resulting from the movement of this compliance (compliant deformation);

d. an interface to the subject using said apparatus to facilitate the transfer of an arbitrary wrench in said degree of freedom to said subject.

In another embodiment of the present invention, said sensors are position sensors or force sensors.

In a further embodiment of the present invention, said multidirectional trunk support system comprises:

a multidirectional elastic decoupling system; having three motor-driven, actuated linear modules, along the horizontal, orthogonal axes X and Y, the vertical axis Z of an X,Y,Z Cartesian frame and one motor-driven actuated rotating module around said vertical axis Z, said axes defining four degrees of freedom; wherein said actuated linear modules are simultaneously decoupled through a suspension system with compliant elements directed in each of the said four degrees of freedom;

ii. a parallel Delta kinematic system to prevent tilting;

Optionally, the apparatus according to the present invention can be equipped with robotic legs.

Any type of position sensor (rotary or longitudinal) or force sensor can be used. In one embodiment of the present invention, said sensors are selected from the group consisting of contact-free magnetic encoders, potentiometers and laser. It is intended that for the purposes of the present invention any kind of suitable sensor can be used according to the knowledge of the person skilled in the art. For example, in said apparatus four contact-free magnetic encoders are located in the joints of said Delta system.

According to another object of the present invention, said apparatus also comprises a computer communicating with said modules and acquiring information coming from said encoders, optionally exchanging information with a second computer running a user interface.

In an embodiment of the present invention, in said apparatus, said motor-driven actuated modules provide a constant-force mode independently from each other.

In an embodiment of the present invention, in said apparatus, said motor-driven, actuated linear modules along said horizontal, orthogonal axes X and Y, and said motor-driven actuated rotating module around said vertical axis Z provide a transparent mode and said motor-driven, actuated linear module along said vertical axis Z provides a constant-force mode.

In another embodiment of the present invention, in said apparatus, a constant force mode can be used in all directions (mainly X, Y, Z), in particular in the training mode.

In a further embodiment of the present invention, all modules can also be actuated in a variable-force mode (e.g. gate-phase dependent support).

The apparatus according to the present invention is used for the rehabilitation (including restoring voluntary control of locomotion) in a subject suffering from neuromotor impairment, wherein said neuromotor impairment is, for example, selected from the group consisting of partial and total paralysis of limbs.

As it will be apparent from the foregoing description, in the unitary concept of the present invention, based on the combination of the multidirectional trunk support system and the device for epidural electrical stimulation, a cocktail comprising a combination of agonists to monoaminergic receptors can be used to enhance the recovery of voluntary control of locomotion by the subject in need of said apparatus. In this sense, another object of the present invention is a pharmaceutical composition comprising a combination of agonists to 5HT1A, 5HT2A/C, 5HT7, and DA1-like receptors for use in restoring voluntary control of locomotion in a subject suffering from a neuromotor disorder.

Another object of the present invention is a pharmaceutical composition comprising a combination of agonists to monoaminergic receptors, in particular to serotoninergic, dopaminergic and adrenergic receptors for use in restoring voluntary locomotion in a subject suffering from a neuromotor impairment.

According to some embodiments of the present invention, said neuromotor disorder is selected from the group consisting of spinal cord injury and the consequences of stroke.

Another object of the present invention is a method for restoring voluntary control of locomotion in a subject suffering from a neuromotor disorder comprising:

e. using the apparatus disclosed above;

f. providing electrical stimulation; in particular to the site of the neuromotor lesion, more in particular to the site of the spinal cord lesion, optionally administering a pharmaceutical composition comprising a combination of agonists to monoaminergic receptors as disclosed above.

In the context of the present invention, the above method is not intended as the steps a) and b) must be carried out one after the other, but they are used according to the teaching of the present invention, in particular electrostimulation with the device for epidural stimulation can be set in different moments of the method and the apparatus can even be used alone, after the epidural stimulation has fired the spinal cord neurons and established a communication with the brain.

In an embodiment of the present invention, the method for restoring voluntary control of locomotion also comprises providing said subject with a treadmill exercise; before using the above-disclosed apparatus and applying epidural electrical stimulation.

Another object of the present invention is a method for operating the above-disclosed apparatus comprising the following steps:

g. evaluating mode, wherein the apparatus provides support against gravity by means of the motor-driven actuated module along the vertical axis Z in a spring-like condition or in a reduced gravity condition;

h. enabling mode, wherein the apparatus provides propulsive and/or postural assistance with a forward movement at constant speed by means of the motor-driven actuated module along the horizontal axis X, while the motor-driven actuated module along the vertical axis Z provides constant-force vertical support as a percentage of the body weight and the motor-driven actuated module along the horizontal axis Y and the motor-driven actuated rotating module around said vertical axis Z provide stiff support in the lateral directions;

i. training mode, wherein the apparatus provides postural support against gravity by means of the motor-driven actuated module along the vertical axis Z, the motor-driven actuated module along the horizontal axis X is set transparent, the motor-driven actuated rotating module around said vertical axis Z is set stiff or transparent, and the motor-driven actuated module along the horizontal axis Y is set stiff or transparent.

In an embodiment of the present invention in the above method, principal component (PC) analysis is performed on gait cycles.

Advantageously, the present invention provides an apparatus which solves the problem of hiding the inertia of massive robotic structure of the prior art and effectively solves the main issues associated with existing support systems, such as unidirectional trunk support, high inertia, or treadmill-restricted stepping.

Moreover, the apparatus herein disclosed can provide an objective evaluation of the complexity of gait and stepping forming the locomotion function. The apparatus can also provide finely tuned enabling and training programs in a rehabilitation process.

The present invention will be now disclosed in detail also by means of figures and examples, in an exemplary embodiment of the present invention on laboratory animals. The system can be scaled up to humans.

In the figures

FIG. 1: shows a perspective view of an exemplary embodiment of the robotic interface of the present invention. The actuated Degrees of Freedom (X, Y, Z, (p) are represented with arrows. The subject using the apparatus is connected to it by a suitable means, for example a skin-like jacket attached to a back plate at the trunk level. The subject will bear also the device for epidural electrical stimulation, said device being positioned according to well-known methods.

Figure 2:
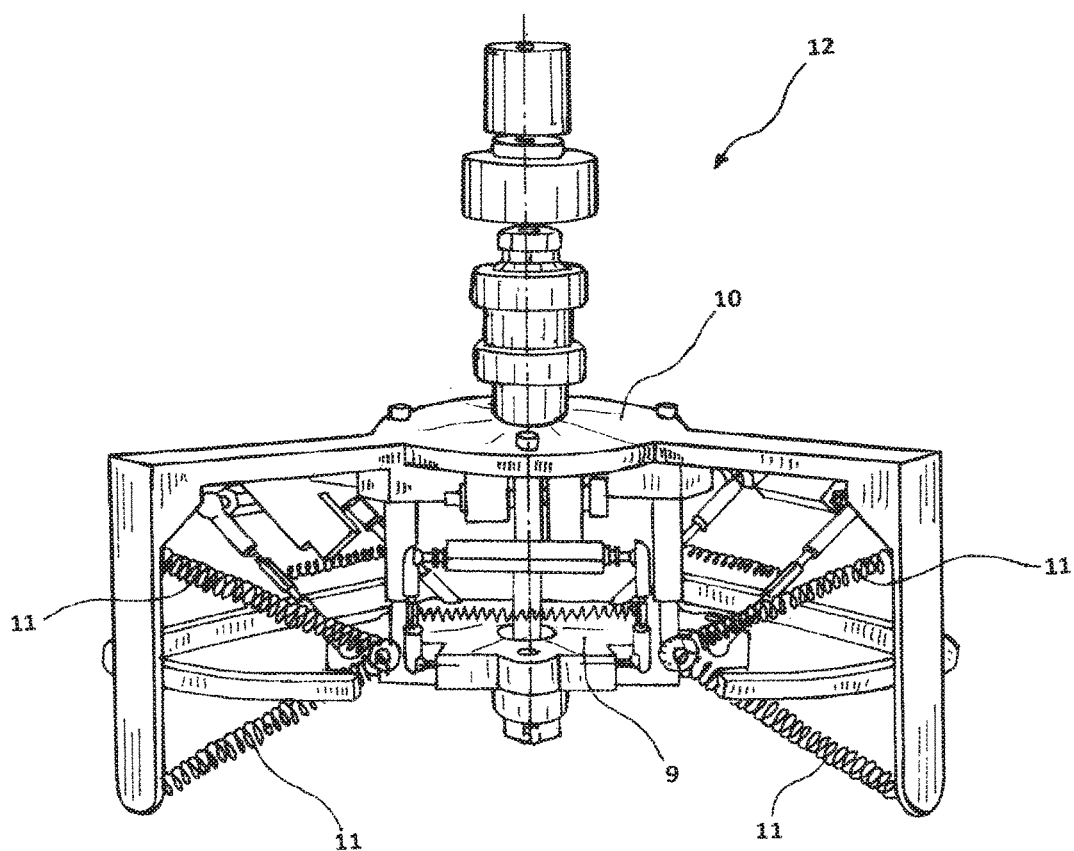

FIG. 2 shows a detailed view of the multidirectional elastic decoupling system according to an embodiment of the present invention.

Figure 3A:
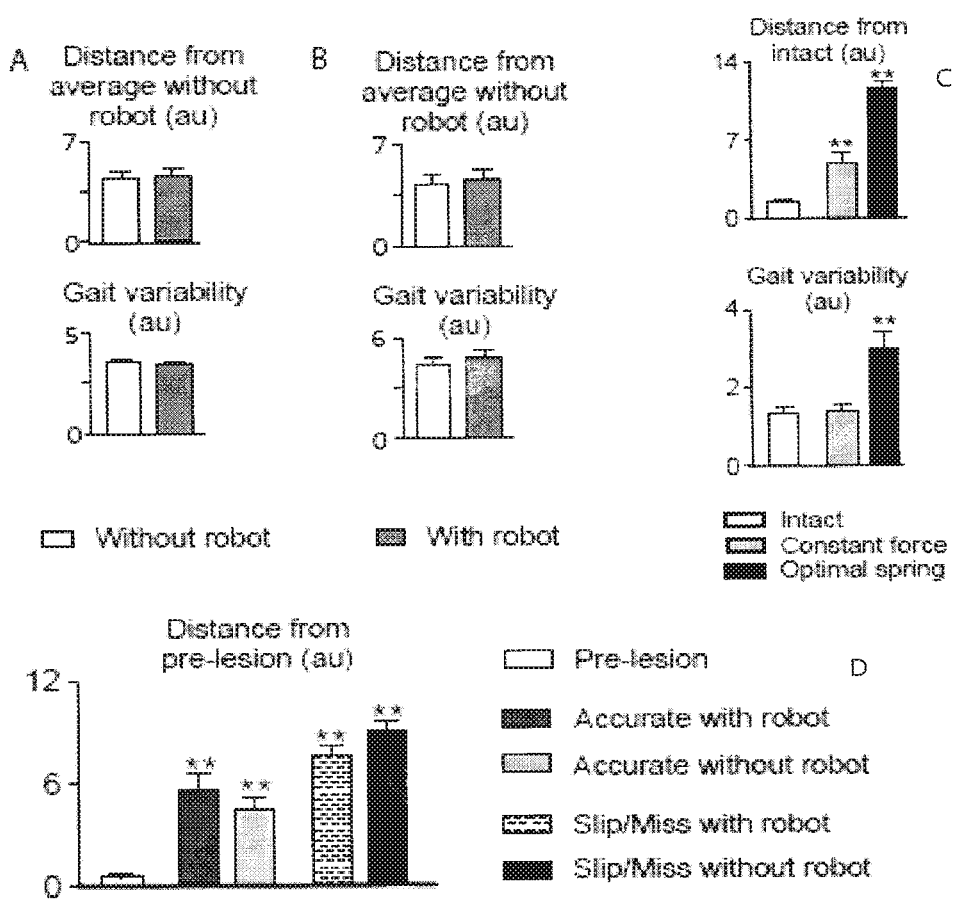
Figure 3B:
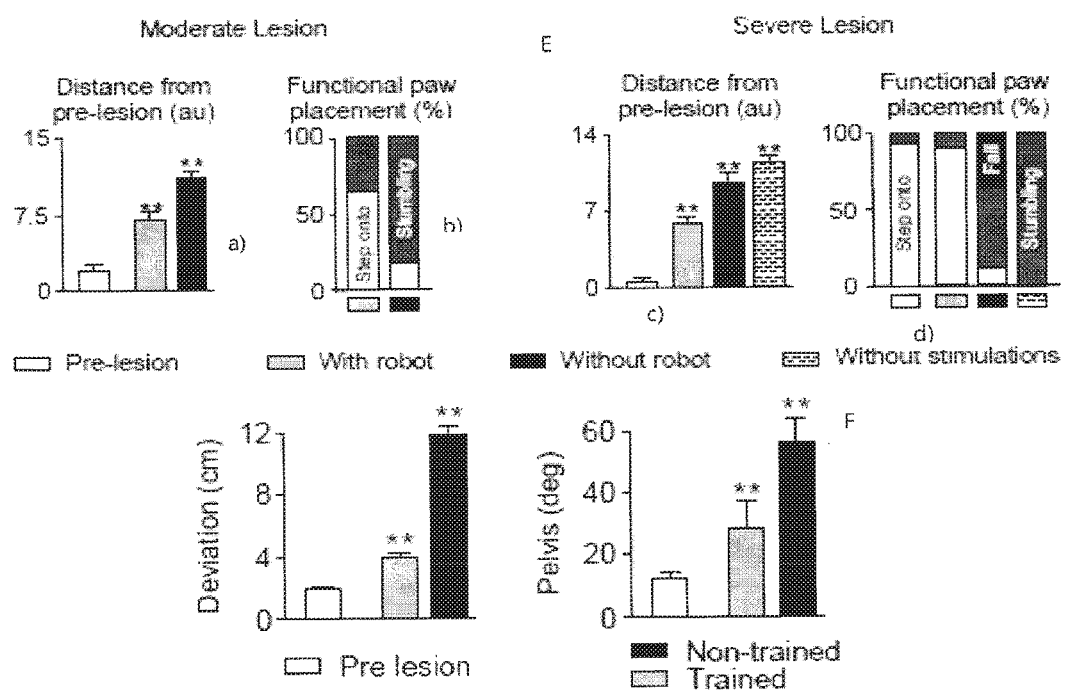

FIGS. 3A and 3B show bar graphs reporting the average (n=7 rats) 3D distance between conditions (distance for each rat from mean of all gait cycles without robot) (A, upper graph) as well as 3D dispersion (gait variability) (A; lower graph); 3D distance between conditions (B, upper graph) and PC analysis of gait during locomotion along a ladder (B, lower graph). a.u. arbitrary unit. Error bars, S.E.M.; bar graphs reporting the average distance from intact rats (C, upper graph) as well as gait variability computed through PC analysis (a.u. arbitrary unit) in the robotic interface in an assessment of pattern generation and balance. (C, lower graph); bar graph reporting the average (n=5 rats) 3D distance from pre-lesion trials. ( significantly different at p<0.01 from all the pre-lesion condition) of an experiment with the robotic postural neuroprosthesis to enable skilled motor control after cortical stroke (D); graphs relating to distance from pre-lesion a), percentage of steps accurately positioned onto the staircase b) (white bar: step onto, grey bar: stumbling); distance from pre-lesion c), percentage of steps accurately positioned onto the staircase d) (white bar: step onto, black bar: fall, grey bar: stumbling) (a.u. arbitrary unit. Error bars, S.E.M. : significantly different at p<0.01 from the pre-lesion condition. The bar links conditions that are statistically different at p<0.01) of an experiment with the robotic postural neuroprosthesis to enable coordinated locomotion on a staircase after moderate and severe SCI) (for all graphs: white: pre-lesion, grey: with robot, black: without robot; dashed: without stimulations) (E); bar graphs reporting the averaged distance between each locomotor trajectory and the optimal trajectory (left); maximum deviation of the pelvis segment with respect to the heading vector (right). (Error bars, S.E.M. **: significantly different at p<0.01 from all the other non-marked conditions) of an experiment of training enabled by the robotic postural neuroprosthesis to restore equilibrated steering in rats with a severe SCI (F).

Figure 4:
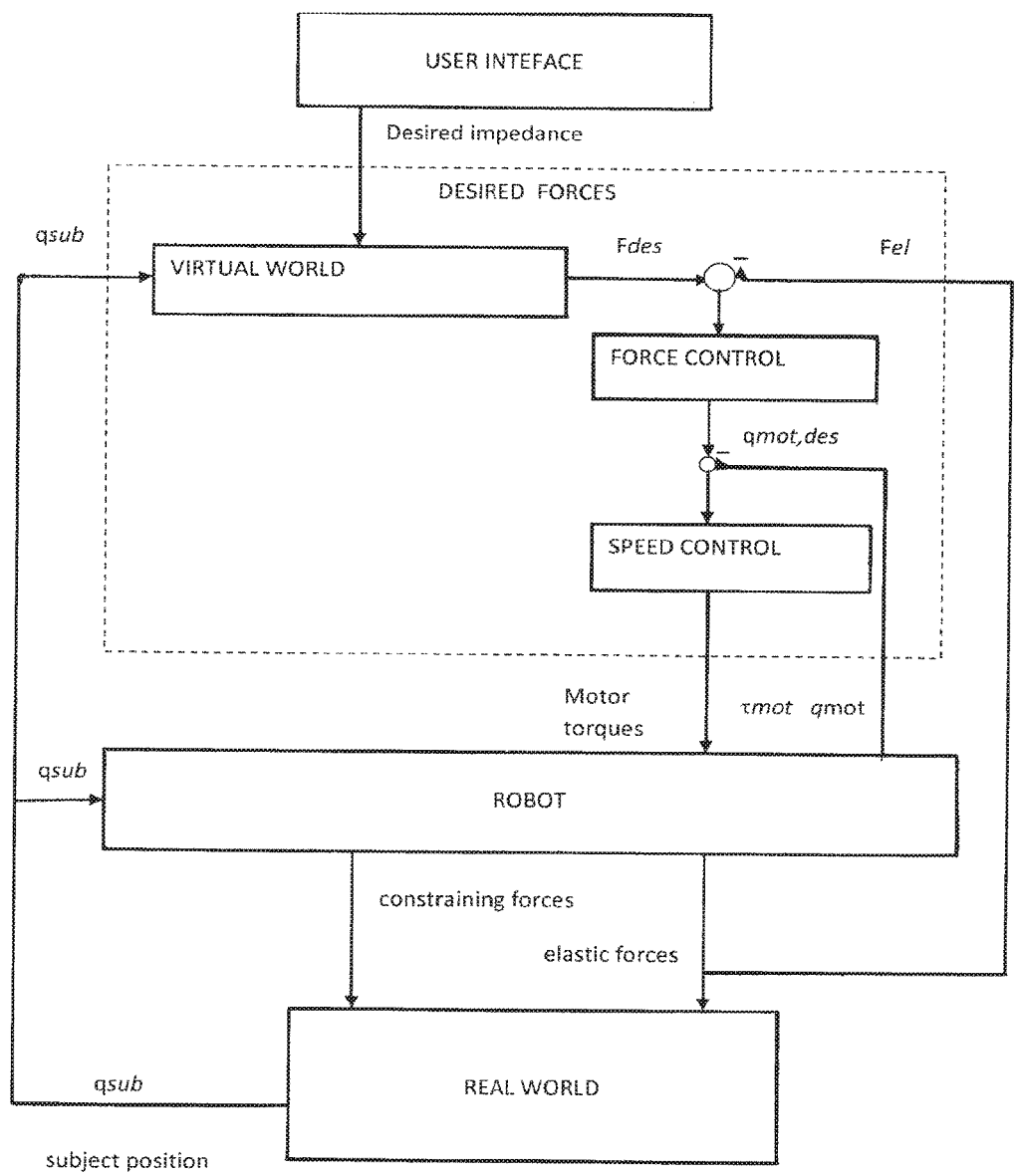

FIG. 4: is a technical description of the robotic interface and control schemes.

DETAILED DESCRIPTION OF THE INVENTION

According to the general concept of the present invention, the goal of achieving voluntary control of locomotion has been made possible by the essential combination of a multidirectional trunk support system with a device for epidural electrical stimulation. In principle, any kind of well-known multidirectional trunk support system and any kind of device for epidural electrical stimulation are suitable to carry out the present invention. The foregoing description will provide details of some embodiments also aimed at improving certain aspect of the invention.

Conveniently, said multidirectional trunk support system provides support to said subject against gravity.

In a preferred embodiment of the present invention, said multidirectional trunk support system comprises a robotic interface having end effectors with n actuated degrees of freedom; means integrated in or attached to said robotic interface to provide compliant/elastic or viscoelastic behavior at said robot's end effectors in said degrees of freedom; sensors to measure the movement of said end effectors resulting exclusively from this compliance and an interface to the subject using said apparatus to facilitate the transfer of an arbitrary wrench in said degree of freedom to said subject.

According to the present invention, the robotic interface has at least 1, preferably at least 2, more preferably at least 3, even more at least preferably 4 degrees of freedom. Means to be integrated in or attached to said robotic interface to provide compliant/elastic or viscoelastic behavior at said robot's end effectors in said degrees of freedom are well known in the art and do not need particular description here, as well as the above-mentioned sensors and the interface.

In order to solve the problem of hiding the inertia of the massive robotic structure, the robotic interface of the present invention is provided with a multidirectional elastic decoupling system (also indicated as multidirectional trunk support system) that renders the robot transparent. This robotic interface effectively solves the main issues associated with existing support systems, such as unidirectional trunk support, high inertia, or treadmill-restricted stepping. The present invention provides an apparatus in the form of a robotic interface, which continuously and independently assists or perturbs propulsion and balance along n, preferably four, degrees of freedom (DoF) while the subject using or being assisted by said interface is progressing overground within a large workspace. In particular, the present invention provides said apparatus as a means for the rehabilitation of a subject suffering from injured locomotor system, especially due to neuromotor impairment, in particular suffering from partial or total paralysis.

In a first embodiment, said robotic interface is used in the rehabilitation of a subject suffering from spinal cord injury (SCI).

In a second embodiment, said robotic interface is used in the rehabilitation of a subject suffering from the aftermath of a stroke.

Advantageously, said robotic interface is able to evaluate, enable, and train pattern generation and balance during walking under natural conditions encompassing a broad spectrum of locomotor behaviors with advanced capacities.

In one embodiment of the present invention, said multidirectional trunk support system comprises:

a multidirectional elastic decoupling system; having three motor-driven, actuated linear modules, along the horizontal, orthogonal axes X and Y, the vertical axis Z of an X,Y,Z Cartesian frame and one motor-driven actuated rotating module around said vertical axis Z, said axes defining four degrees of freedom; wherein said actuated linear modules are simultaneously decoupled through a suspension system with compliant elements directed in each of the said four degrees of freedom;

ii. a parallel Delta kinematic system to prevent tilting;

Now referring to FIG. 1, an exemplary embodiment of the robotic interface of the present invention comprises:

(i) a serial robotic module consisting of three translational axes defining a Cartesian frame (x, y, z), as well as one rotational axis (φ) and shown as the general reference (1);

(ii) a parallel Delta kinematic system which prevents tilting, and allows measurement of the subject's position and shown as the general reference (2);

(iii) a suspension system with springs directed in each of the four DoFs of the serial structure (FIG. 2) in order to decouple the inertia of the massive robotic structure from the end-effectors. This suspension system capitalizes on the high-performance of series elastic actuators for the realization of transparently behaving haptic devices (Pratt, G. A., et al. Stiffness Isn't Everything. in *International Symposium on Experimental Robotics (ISER)* (Springer, Stanford, USA, 1995); Vallery, H., et al. Compliant actuation of rehabilitation robots—Benefits and limitations of series elastic actuators. *Ieee Robot Autom Mag* 15, 60-69 (2008)).

The robotic interface of the present invention advantageously allows real-time control of body translations (propulsion) and body weight support (BWS) (balance) along four independent DoFs that can be continuously adjusted, i.e. from stiff position control to transparent, zero-force control.

In more detail and referring to FIG. 1, item (i) of the robotic system of the present invention has the scope to provide adjustable trunk support along 4 independent degrees of freedom (DoF).

Three motor-driven, actuated linear modules (3, 4, 5) are provided. These kinds of modules are commercially available, see for example CKK 20-145, CKK 15-110 and CKK 12-90 (Bosch Rexroth AG) and define a large Cartesian workspace capable of translating the subject in X, Y, Z directions. The first two axes (FIG. 1, (X) and (Y)), which are used for movements in the horizontal plane, cover a large area (6) estimated to be sufficient for the subject using the interface. The third axis (FIG. 1, (5, Z)) provides the subject with support against gravity, and allows vertical movements over a sufficient range for the rehabilitation purpose. At the extremity of this Cartesian structure, a fourth motor (7), of the type available on the market, for example RE25, Maxon motor AG, Sachseln, Switzerland, actuates rotations (for example 300 deg) about the vertical axis (FIG. 1, φ). This serial configuration provides a large workspace in which forces can be applied to the subject while preventing inclinations about the horizontal directions.

The assembly of the four motor-driven modules can be firmly supported by a suitably built framework (FIG. 1, (8) showing only one support for module 4. For simplicity, other parts of the framework are not shown, since the can be constructed in different ways, according to common general knowledge), wherein the motor-driven modules can translate along the X, Y and Z axes. The framework can provide frame members suitable to support the motor-driven modules and allow movement along their direction. For example, frames in the form of rails can be provided for the modules (3), (4) and (5), upon which the modules are mounted in a conventional way. A vertical structure is used to support the motor driven module (5), arranged in a way that it can move along the vertical axis Z. The way of mounting the three modules and the framework supporting them is conventional and within the capacities of the person of ordinary skill in this field.

The area (6) can be provided with different means for training the subject in need of rehabilitation, for example straight or differently curved paths, obstacles, ladders, treadmill.

When desired, in order to provide a highly flexible robotic system capable of guiding the subjects along any desired trajectory, but which also can behave transparently, i.e. allowing the patients to walk freely in the entire workspace without "feeling" the robot, the interaction forces between the subject and the robot have to be reduced to a minimum. The inertia of the robot is significantly larger than the mass of the subject using it.

Typically, using conventional stiff force sensors and force control, the inertia of the robot could not be hidden from the subject due to theoretical stability limitations to force control (Colgate, E. & Hogan, N. An Analysis of Contact Instability in Terms of Passive Physical Equivalents. Proceedings—1989 Ieee International Conference on Robotics and Automation, Vol 1-3, 404-409 (1989)). Consequently, a direct coupling between the robot and the subject would yield substantial interaction forces that will interfere with the natural movements of the same. To hide the inertia of a robotic structure from a substantially lighter interacting subject, Pratt, G. A., et al. (Stiffness Isn't Everything. in *International Symposium on Experimental Robotics (ISER)* (Springer, Stanford, USA, 1995)) proposed to couple an actuator to a subject via a compliant element; this configuration is called a Series Elastic Actuator (SEA). Moreover, interaction forces and torques can be measured directly by monitoring the deformation of the compliant element. However, the concept of SEA has so far only been used for individual actuators, i.e. a single DoF.

In an embodiment of the present invention, to optimally exploit the SEA concept for the robotic interface of the present invention, all four actuated modules need to be decoupled simultaneously, requiring that all deformable elements are as close as possible to the subject.

It has been found (see FIG. 2) that the problem is solved by providing a lightweight, low-friction, compliant module consisting of a base platform with three protruding legs forming a cage (10)), a spring-suspended platform (9) within this cage, and a Delta structure that constrains the unactuated DoF (i.e. tilting of the subject).

Referring to FIG. 2 the suspended platform (9) is connected to the cage (10) via six linear springs (11, one couple is not shown, standing behind the cage), said springs are calibrated on the weight of the subject under treatment (for example for a small animal, such as a rat or mouse the following settings can be adopted: angle in the horizontal plane, 120 deg angle; stiffness, 112 N/m for upper springs, 57 N/m for lower springs). An additional spring pair (not shown) is attached to the rotating shaft in the center of the suspended platform (9), providing the elastic decoupling about the vertical axis. Together, this configuration decouples the inertia of the serial module from the suspension platform in the 4 actuated DoFs.

The Delta structure (12) allows the measurement of the displacements of the suspended platform, and thereby the deflection of the springs along each DoF, providing an inexpensive way of measuring interaction forces or torques.

In order to make measurements of interaction forces, any known apparatus can be used. In one embodiment of the present invention, four contact-free magnetic encoders (sensors) (commercially available, for example from 12-bit, Austria microsystems, Austria) are located in the joints of the Delta structure. The position of the end-effector with respect to the serial robot is calculated by combining information from these angular sensors and a forward kinematic model of the Delta structure. The relative position of the platform encodes the spring lengths, and thereby the interaction forces and torques that are derived from the linear spring characteristics.

These forces and torques are used in the force control loop of the robot. The control strategy is implemented in MATLAB/Simulink and executed in real-time on a desktop computer running xPC target (sampling rate, 1 kHz). This computer communicates with the motor drives of the actuators and acquires information coming from the sensors. It also exchanges information with a second computer that runs a user interface for online changes of the control parameters for the robot.

The SEA-based elastic decoupling allows to set extremely high control gains without affecting stability. Due to the use of the multidimensional SEA, this inertia only dominates the perceived dynamics for low-frequent excitations (Vallery, H., et al. Compliant actuation of rehabilitation robots—Benefits and limitations of series elastic actuators. Ieee Robot Autom Mag 15, 60-69 (2008)), for which inertial forces are low. For high-frequency excitations, which are generally associated with reduced amplitudes of motion, the physical properties of the springs dominate the response, also leading to low forces. Consequently, the subject mainly feels the inertia of the suspended platform.

The robotic interface thus combines the advantages of serial kinematics (large workspace), parallel kinematics (low inertia), and series elastic actuation (compliant interactions) extended in multiple dimensions. Together, this novel robotic arrangement affords the real-time control of body translations (propulsion) as well as body weight support (BWS) conditions (balance) along four independent DoFs within a configurable environment.

Referring to FIG. 4, the control of the robotic interface is further disclosed.

User Interface

A user-friendly GUI (Graphical user interface) is implemented in, for example, MATLAB/Simulink (The MathWorks, CA) or other similar programs. The interface allows the user to create a virtual environment (shown as "virtual world" in FIG. 4) in which the applied forces or the end-effector position can be adjusted for each single actuated DoF of the robot. For example, the user can independently set any of the 4 actuated axes to behave transparently. Concomitantly, the vertical axis provide a constant force that is proportional to the subject's body weight, as for supporting the subject against gravity. The axes can also be configured to be stiff in order to prevent lateral fall or to guide the subject along a user-defined trajectory. Alternatively, the user can control the displacement of the end-effector (position control), as for pushing the subject in a given direction, or along a user-defined trajectory. Finally, the user can introduce sudden changes in the virtual environment (arbitrary wrench). For example, a user-defined perturbation can be superimposed onto any control scheme based on external triggers or the position of the subject in the real world. For example, the user can create a virtual environment for a straight path for the subject, or a path comprising at least a bend, or a path comprising a stretch of irregularly spaced horizontal pins (supports), or a straight gait at constant velocity, or a straight path in which lateral movements are induced, or to set a path comprising climbing and descending a stair. The four motor-driven actuated modules can be set by the user in different modes: stiff (100% constant force), transparent (unfelt by the subject), constant force (%) and constant velocity.

Versatile Impedance Control Implementation

Referring to FIG. 4, an impedance control scheme is implemented that can adjust the force exerted by each actuated DoF of the robotic interface independently in real-time (1 kHz). The controller is cascaded: an outer loop processes the position of the subject with respect to the virtual environment; for example a world with guiding walls or gravity-reduced conditions. An algorithm translates the virtual environment defined by the user into a vector $$F_{des} = \begin{pmatrix} F_{x,des} \\ F_{y,des} \\ F_{z,des} \\ \tau_{rot,des} \end{pmatrix}$$

of desired forces and torques. A force controller adjusts the desired motor speeds $q_{mot,des}$ sent to the drives of the modules along the four degrees of freedom (DOF) based upon the error between the desired forces and the forces measured through spring deflection of the decoupling system. An inner speed controller ensures that the actual motor speed $q_{mot}$ tracks the desired motor speed by commanding appropriate actuator torques $\tau_{mot}$. The outer loops run on a Matlab xpc real-time operating system. The speed control runs on the actuator drives.

Robot

Cartesian Positioning System:

The robot consists of an actuated Cartesian positioning system that allows translations of the subject in the horizontal plane (x,y) while providing vertical support (z). An additional motor at the end-effector of this serial structure actuates rotation (φ). This serial configuration provides a large workspace in which forces can be applied to the subject in 4 DoFs.

Force Module:

To hide the inertia of the massive positioning robot and to measure the extremely small interaction forces between the robot and the subject using the robot, the present invention provides a novel force module based on a "Series Elastic Actuator" (SEA). A SEA is composed of an actuator that is complemented with a passive compliant element in series. This compliance improves force control performance and effectively decouples actuator inertia to achieve a transparent interface. In the force module according to the present invention, the SEA concept is extended to 4 DoFs by providing multidimensional compliance at the end-effector of the positioning system.

Kinematic constraints for unactuated DoF: A mechanical "Delta" linkage prevents the subject from tilting in the 2 unactuated DoF, leading to constraining forces $F_C$. The Delta structure also provides the means of measuring the end-effector position (subject position $q_{sub}$) and subsequently the interaction forces $F_{el}$ between the robot and the subject, see equation above, where in this case $F_{el}$ takes the place of $F_{des}$ and each variable is el, in place of des.

Elastic Decoupling of Actuated DoF:

The compliance for the residual DoFs is achieved by multiple linear springs attached to the suspended platform and by an additional spring pair attached to the rotating shaft within the platform.

Real World

The subject is positioned in a custom-made apparatus for holding the subject, for example a harness or a skin-like jacket, preferably made of light fabrics. A closure, such as a Velcro strip, allows attachment of the subject onto a back plate with a rigid bar coming from the robot end-effector. The subject's position and the interaction forces with the robot are fed back to the impedance controller.

Locomotor capacities of intact and motor impaired subjects can be evaluated for example in a number of tasks. a. Locomotion along a straight horizontal runway. b. Locomotion along a 90 deg-curved horizontal runway. c. Locomotion along a straight horizontal ladder with irregularly spaced rungs. d. Locomotion along a straight horizontal runway, where the robot propels the subject forward at a constant velocity. e. Lateral perturbation introduced during continuous locomotion along a straight horizontal runway (task a). f. Continuous locomotion on a motorized treadmill belt. g. Locomotion along regularly spaced steps on a staircase. For each task, the degree of compliance is adjusted for each translational and rotational axis independently. Control strategies include: stiff control, zero-force control, adjustable constant-force (constant-force set to a percentage of body weight), and constant-velocity (position control).

The results of the exercises performed with the robotic interface of the present invention are elaborated with a proper statistical method. In a representative embodiment carried out on laboratory animals (rats) the set of experimental data is processed in a multi-step statistical analysis, applied for all the experiments herein described. Step 1: For all the experimental conditions, kinematic, kinetic and EMG data during continuous locomotion are collected using a recording system. Step 2: A large number of parameters is computed, providing a holistic quantification of gait features. The analytic procedures and computations are detailed in Courtine, G., et al. Transformation of nonfunctional spinal circuits into functional states after the loss of brain input. *Nat Neurosci* 12, 1333-1342 (2009), Musienko, P., et al. Controlling Specific Locomotor Behaviors through Multi-dimensional Monoaminergic Modulation of Spinal Circuitries. *J Neurosci* 31, 9264-9278 (2011). Step 3: We applied a principal component (PC) analysis on all the variables (n=144) computed from all the gait cycles from all the rats and experimental conditions. Gait cycles are represented in the new 3D space created by the 3 first PCs (explained variance, 39%). Least-squares spheres are traced to emphasize the overlap between gaits performed without and with robot. This analysis constructs new variables, i.e. PC, that linearly combine the original variables and maximize the amount of explained variance for each successive PC. Due to the high degree of correlation between gait parameters during locomotion, a few PCs are sufficient to explain a large proportion of the variance. Step 4: The gait cycles can be represented in the new "denoised" space created by PC1-3. In the proposed embodiment, data points associated with each experimental condition cluster in a well-defined location, indicating that the rats exhibited intervention-specific gait patterns. Typically, PC1 powerfully differentiates gait cycles from intact rats (or pre-lesion), altered gaits from rats with SCI or stroke, and the improvement of locomotion with the robotic interface. In some instances, PC2 captures an additional feature. In the proposed embodiment, PC2 is related to specific features of the intervention compared to intact and no intervention. In order to provide a straightforward representation of differences between conditions, we applied a least square elliptic fitting to the 3D data points. Step 5: To quantify the quality of gait performance, we measured the 3D geometric distance between the averaged location of gait cycles from each rat in a given condition and the average location of all gait cycles from all intact (or pre-lesion) rats. For each rat and condition, we also measured (in au, arbitrary units) the 3D dispersion of gait cycles to provide a measure of gait variability. Step 6: The scores (position of gait cycles in the PC space) reveal which conditions are differentiated along each PC. Step 7: We then extracted the factor loadings, i.e. correlation between each variable and each PC. We selected the PC of interest based upon step 6, and regrouped the variables with the highest factor loading (|value|>0.5, $p<0.05$) into functional clusters, which we named for clarity. Variables that load on the same PC correlate with each other. For instance, in one embodiment, improvement of hindlimb locomotion directly correlates with improved postural control. Step 8: To provide a more classic representation of differences between conditions, we generated histogram plots for one variable per extracted functional cluster.

In a preferred embodiment of the present invention, the motor-driven actuated modules are used in the constant-force mode, which leads to improved locomotor performance compared to spring-like support in rats with complete SCI.

Operating Modes

The robotic interface according to the present invention can operate in three distinct modes: 1) evaluation mode for the evaluation of motor pattern generation and balance; 2) enabling mode for the robot-enabled motor control after neuromotor impairments; 3) training mode for the robot-enabled training, this latter mode is useful for rehabilitation of a subject, for example suffering from a paralyzing SCI.

1) Evaluation Mode

The robotic interface according to the present invention is capable to assess motor pattern generation and balance, thanks to a constant force support.

Most BWS systems rely on passive spring mechanisms, which provide a support against gravity that is proportional to the subject's vertical position. Although special kinematic configurations can achieve position-independent, constant force support (Nessler, J. A., et al. A robotic device for studying rodent locomotion after spinal cord injury. *IEEE transactions on neural systems and rehabilitation engineering: a publication of the IEEE Engineering in Medicine and Biology Society* 13, 497-506 (2005)), there is a problem in that these passive systems do not compensate for rapid movements.

Advantageously, in this evaluation mode embodiment, the robotic system according to the present invention can apply well-controlled, arbitrary vertical force profiles that are capable of emulating spring-like conditions or a reduced gravitational environment. In fact, when compared to spring-like BWS, the constant-force BWS according to the present invention markedly improves the quality and consistency of gait features and promotes locomotor patterns that converge towards those of healthy subjects.

The evaluation mode according to the present invention provides heuristic conditions to assess motor pattern generation and balance following neuromotor impairments.

2) Enabling Mode

According to the present invention, the robotic interface can be used as a propulsive and/or postural neuroprosthesis that provides adjustable assistance to propel the body forward and to restore postural orientation and stability.

It is well known that electrical and pharmacological stimulations enable locomotion in subjects, and potentially in humans (Harkema et al. Lancet), with severe SCI, but the subjects fail to produce the necessary forces to propel their body forward overground. Instead, they display tonic activity in extensor muscles, behaviorally apparent as standing. To compensate for the lack of propulsion, the robotic interface according to the present invention acts as a propulsive neuroprosthesis that moves the subjects forward at a constant speed while providing constant-force vertical support as a percentage of the body weight, which is adjusted according to the needs of the subject and the rehabilitation program (for example 60+/−10% of BWS). When initiating the robotic guidance, the subjects smoothly transition from quiet standing to continuous locomotion. Rhythmic movements arrest instantly when the propulsive neuroprosthesis stops translating the subject forward.

Enabling mode is now illustrated in an exemplary embodiment on a laboratory animal.

Rats with unilateral, left-sided cortical stroke display significant impairments in contralesional paw placement when crossing a horizontal ladder with irregularly-spaced rungs (Zörner, B., et al. Profiling locomotor recovery: comprehensive quantification of impairments after CNS damage in rodents. Nature methods 7, 701-708 (2010)). The relative positioning of the contralesional hindpaw with respect to two successive rung positions was evaluated over all the trials from all the rats without and with constant-force robot support. Evaluation was made through stick diagram decomposition of hindlimb motion during the trial with and without robot. Hindlimb oscillations and EMG activity of TA and Sol muscles were registered. The PC analysis (explained variance, 28%) was performed to dissociate accurate steps from missed steps to emphasize that the robot increased the percentage of accurate steps, but had no influences on locomotor strategy per se. The results (FIGS. 3A, A and B) show the average 3D distance from pre-lesion trials. (**: significantly different at $p<0.01$ from all the pre-lesion condition).

These deficits have been attributed to the loss of visuomotor control, which heavily relies on the damaged motor cortex (Drew, T., Andujar, J. E., Lajoie, K. & Yakovenko, S. Cortical mechanisms involved in visuomotor coordination during precision walking. *Brain Res Rev* 57, 199-211 (2008)). Impaired equilibrium maintenance may also contribute to the alteration of skilled locomotion after a cortical stroke. The robotic interface according to the present invention acts as a postural neuroprosthesis.

In this embodiment of enabling mode, the robot provides a constant-force support in the vertical direction (z axis, 27±4% of BWS) and stiff support in the lateral directions (y and rotational axes). The robotic postural neuroprosthesis instantly improved the subjects' ability to position their contralesional limb accurately onto the irregularly spaced rungs of the ladder. Statistical analyses showed that the robot significantly decreases the number of miss/slip, which correlated with improved postural stability.

Therefore, the robotic postural neuroprosthesis according to the present invention enables motor control in subjects with locomotor impairment, in particular due to SCI or stroke.

Unexpectedly, the enabling mode of the robotic interface instantly restores locomotor capacities across a wide range of natural walking behaviors after moderate to severe neuromotor impairments.

3) Training Mode

In the embodiment of the training mode, the robotic interface enhances functional capacities with repeated practice. According to this mode, the robotic postural neuroprosthesis provides support against gravity (z axis), but is set transparent in the other directions (x, y, and φ axes). Locomotion is enabled, for example by electrical and optionally pharmacological stimulations. The training mode of the robotic interface significantly improves locomotor capacities. In one embodiment of the present invention, this robotic interface is suitable for training program in subjects with paralyzing locomotor disturbances, such as SCI.

When acting as a postural or propulsive neuroprosthesis, the robotic interface of the present invention instantly enables unexpected locomotor capacities in affected subjects.

There are correlations between robotically restored multidirectional trunk balance and improved lower limb motor control. These immediate functional improvements emphasize the importance of expanding current trunk support systems, which, in the prior art are exclusively unidirectional, to multiple dimensions. Likewise, robotic exoskeletons that provide multidirectional support against gravity enable enhanced upper limb recovery in stroke survivors (Kwakkel, G., Kollen, B. J. & Krebs, H. I. Effects of robot-assisted therapy on upper limb recovery after stroke: a systematic review. Neurorehabilitation and neural repair 22, 111-121 (2008)) and improved locomotion in humans with partial SCI (Duschau-Wicke, A., Caprez, A. & Riener, R. Patient-cooperative control increases active participation of individuals with SCI during robot-aided gait training. Journal of neuroengineering and rehabilitation 7, 43 (2010)).

The robotic postural neuroprosthesis of the present invention not only provides multidirectional trunk support but also restores limb and trunk orientation. In consequence, the flow of stretch- and load-related afferent input from hip and ankle joints, which play an essential role to coordinate locomotion (Pearson, K. G. Generating the walking gait: role of sensory feedback. Prog Brain Res 143, 123-129 (2004)), come closer to a normal range. It is underlined that the recovery of crucial sensory feedback and its task-specific modulation significantly contributes to re-establishing gait control. For example, the robotic postural neuroprosthesis enables enhanced hip extension during stair climbing compared to horizontal locomotion. This information appears sufficient to mediate increased step height and accurate foot placement onto the staircase. Similarly, side-dependent modulation of load- and stretch-sensitive receptors from ankle and trunk muscles during curve-walking results in the production of asymmetric force patterns that maintain equilibrated steering. To this end, the interface of the present invention is conveniently equipped with sensors to measure forces. These sensorimotor processes are improved with training. Together, these findings confirm and expand current views on the ability of sensory information to act as a source of control for locomotion after the loss of supraspinal influences (Courtine, G., et al. Transformation of nonfunctional spinal circuits into functional states after the loss of brain input. Nat Neurosci 12, 1333-1342 (2009); Harkema, S., et al. Effect of epidural stimulation of the lumbosacral spinal cord on voluntary movement, standing, and assisted stepping after motor complete paraplegia: a case study. Lancet 377, 1938-1947 (2011)). To this respect, the interface of the present invention can be equipped with robotic legs (exoskeletons) attached to the lower limbs (Nessler, J. A., et al. A robotic device for studying rodent locomotion after spinal cord injury. IEEE transactions on neural systems and rehabilitation engineering: a publication of the IEEE Engineering in Medicine and Biology Society 13, 497-506 (2005)) to ensure appropriate task-specific sensory feedback during rehabilitation (Edgerton, V. R. & Roy, R. R. Robotic training and spinal cord plasticity. *Brain research bulletin* 78, 4-12 (2009)).

In a different aspect, the present invention relates to a method for restoring voluntary control of locomotion in neuromotor impairment, such as after paralyzing spinal cord injury, as well as to a method for the rehabilitation of a subject suffering from a neuromuscular disturbance in particular partial or total paralysis of limbs, this method achieving voluntary control of movement, comprising applying electrical and optionally pharmacological stimulation and using the above robotic interface in an overground training programme.

In a preferred embodiment, the method according to the present invention comprises a first step of treadmill exercise and a second step comprising an overground training with the robotic interface of the present invention combined with electrical stimulation, optionally combined with pharmacological stimulation.

It is important to note that in the training mode, the subject can gain sufficient control of locomotion that electrical stimulation can be given up and assistance can be provided by means of the robotic interface only.

PC analysis (explained variance, 48%) was applied on all gait cycles and rats. Least square fitting was performed and indexed for each rat independently. Mean values of scores on PC1 for gait cycles were recorded in intact rats and in spinal rats stepping with the same level of spring-like vs. constant force vertical support. Variables with the highest factor loadings on PC1 ($|value|>0.5$, $p<0.05$) were regrouped in functional clusters. Mean values for one variable per functional cluster for intact rats and spinal rats stepping with spring-like vs. constant force vertical support were calculated.

Evaluation of the impact of weight bearing conditions on motor pattern generation in rats with complete SCI was performed. Rats received a complete SCI. After 5 weeks of recovery, the rats received enabling factors to encourage bipedal locomotion on a treadmill (13 cm·s$^{-1}$). 10 gait cycles were recorded for each level of constant-force BWS (40-90%). Locomotion was recorded in healthy rats at 60% of BWS, which is the weight normally carried by the hindlimbs during quadrupedal gait. Representative stick diagram decomposition of hindlimb motion during stance, dragging, and swing for each level of BWS, as well as for an intact rat were obtained. Trajectories of the hindlimb endpoint were traced together with the orientation and intensity of the foot velocity vector at swing onset. The average vertical ground reaction forces (left and right hindlimbs combined) and relative duration of the stance, swing, and drag phases of gait were determined. Relationship between the level of BWS and the degree of gait pattern similarity compared to healthy rats, were measured as the 3D distance from gait cycles in the PC analysis. A second-order polynomial fitting was applied to the data points to highlight the U-shaped relationship between stepping quality and BWS levels. Variables with the highest factor loadings on PC1 ($|value|>0.5$, $p<0.05$) were regrouped in functional clusters. Mean values for one variable per functional cluster under the different levels of BWS were obtained.

The robotic propulsive neuroprosthesis according to the present invention enables coordinated overground locomotion in spinal rats. Spinal rats were positioned bipedally in the robotic interface. The robot was configured to move the body forward at a constant velocity (13 cm·s$^{-1}$) while providing constant-force vertical support. In the stick diagram decomposition of hindlimb motion and limb endpoint trajectories, the traces show angular oscillations of both hindlimbs. To enable hindlimb locomotion, rats received tonic epidural electrical stimulation at spinal segments S1 and L2, as well as a combination of agonists to 5HT1A, 5HT2A/C, 5HT7, and DA1-like receptors. With these stimulations, the spinal rats displayed tonic activity in left and right extensor muscles, and could stand for extensive periods of time. The animals immediately exhibited coordinated plantar stepping with alternation between both hindlimbs when the robot translated the trunk in the forward direction to replace the lost propulsive capacities.

Using the robotic interface of the present invention, the improved balance control with the postural neuroprosthesis correlates with improved hindlimb locomotion and performance during locomotion along a ladder with irregularly spaced rungs in rats with a cortical stroke. The apparatus according to the present invention, namely the robotic interface combined with a device for epidural electrical stimulation and the pharmaceutical composition comprising a cocktail of a combination of agonists to 5HT1A, 5HT2A/C, 5HT7, and DA1-like receptors provides an improved balance control which correlates with improved hindlimb locomotion and performance during locomotion, for example along a ladder with irregularly spaced rungs in rats with a cortical stroke.

PC analysis was applied on all gait cycles recorded along the ladder in all the rats before and 2 days after lesion with and without vertical constant-force robotic support. Accurate and missed steps were both included in this analysis, but undifferentiated in the plot to emphasize the contrast between the conditions with and without robot. Mean values of scores on PC1 were obtained. Variables with the highest factor loadings on PC1 ($|value|>0.5$, $p<0.05$) were regrouped in functional clusters.

Using the robotic interface of the present invention, improved balance control with the postural neuroprosthesis correlates with improved hindlimb locomotion during straight horizontal runway locomotion in rats with moderate and severe SCI.

Stick diagram decomposition of hindlimb motion, hindlimb oscillations, and EMG activity of Sol and TA muscles recorded pre-lesion as well as 10 days after a lateral cervical (C7) hemisection with and without constant-force robotic support were recorded. PC analysis was applied on all gait cycles recorded in all the rats before and 10 days after lesion with and without robotic support. Hindlimb kinematics and EMG activity of MG and TA muscles were recorded pre-lesion as well as 12 days after staggered lateral hemisections without enabling factors (no stimulations) as well as with stimulations without and with constant-force robotic support. PC analysis was applied on all gait cycles recorded in all the rats before and 10 days after lesion without stimulations as well as with and without robotic support. Mean values of the 3D distance between the different experimental conditions and the mean location of pre-lesion gaits in the PC space were calculated. PC1 differentiates actual stepping vs. paralysis, while PC2 highlights the improvement of locomotion with the postural neuroprosthesis.

Using the robotic interface of the present invention, improved balance control with the postural neuroprosthesis correlates with improved hindlimb locomotion during locomotion on a staircase in rats with moderate SCI (lateral cervical (C7) hemisection).

Experiment, evaluation and result analysis were performed as disclosed above.

In a similar manner, the robotic interface of the present invention shows that improved balance control with the postural neuroprosthesis correlates with improved hindlimb locomotion during locomotion on a staircase in rats with severe SCI (staggered lateral hemisections).

Experiment, evaluation and result analysis were performed as disclosed above.

The method of restoring voluntary control of locomotion in a subject suffering from a neuromotor impairment, for example a disorder selected from the group consisting of spinal cord injury and the consequences of stroke, will be now disclosed in detail.

Using the controls of the robotic interface of the present invention, typically, the X-axis (forward direction) is set to behave transparently and the Z-axis to provide a constant force proportional to the subject's body weight. The lateral (Y) and rotational ($\varphi$) axes are maintained stiff to prevent lateral falls. For specific testing and training, the robot can move the subject's trunk forward at a constant velocity. Consequently, the limbs move backward and hip joint angle increase towards extension, thus creating conditions that are similar to stepping on a treadmill. Although performed overground, these stepping movements are still involuntary.

The training consists of a combination of 4 distinct paradigms broadly divided into 3 phases specifically tailored to the subject's performance and training objectives. To enable highly functional motor states, the subject can optionally receive monoamine agonists 10 min prior to training, and dual-site EES throughout the session. Phase (1). The primary objective of the early training phase is to optimize the functionality of lumbosacral circuits. The subject is subjected to treadmill-based training with vertical support. Sensory input elicited by the moving treadmill belt serves as a source of control for limb stepping. Manual assistance is provided in an assist-as-needed manner in order to present appropriate sensory cues to lumbosacral circuitries. At the end of each session, the subject is positioned in the robotic postural interface and encouraged to walk towards a target located in front of him. The robot is configured to establish optimal medio-lateral and vertical weight support. In order to provide contextual information on the requested task, the robot translates the subject forward at a constant velocity. The objective is to force the brain to regain supraspinal control over the electrochemically enabled lumbosacral circuits. Phase (2). As the subject progressively regains the ability to produce voluntary steps, the duration of locomotion overground is gradually increased. The aim is to encourage the repetitive and quantitative activation of lumbosacral circuits by the newly formed intraspinal and supraspinal connections. However, treadmill-restricted training is still practiced daily in order to engage spinal locomotor circuits over consistent periods of time for the maintenance of their functionality. Phase (3). When the subject regains robust hindlimb locomotion overground, complex tasks requiring fine-tuning of hindlimb movements, i.e. stair climbing and obstacle avoidance, are introduced. The goal is to promote enhanced supraspinal contribution in order to restore qualitative control over electrochemically enabled lumbosacral circuits.

A stick diagram decomposition of hindlimb motion is produced together with trajectories of the hindlimb endpoint. The hindlimb is defined as the virtual segment connecting the pelvis to the foot. Vectors representing the direction and intensity of the hindlimb endpoint velocity at swing onset are used to evaluate the progress of rehabilitation. Multi-step statistical analysis of locomotor performance and control strategies is carried out. Step 1: Advanced recordings of hindlimb kinematics during bipedal overground locomotion. Step 2: A large number of variables that provides a holistic quantification of gait is computed. Step 3: Principal component (PC) analysis on all the variables and recorded gait cycles is applied. Step 4: Individual gait cycles in the new "denoised" space created by PC1-3 is then represented. Least square elliptic fitting to easily visualize differences between the subsequent rehabilitation steps is used. Step 5: Locomotor performances are quantified, as the 3D Euclidean distance between the location of gait cycles and the average location of all gait cycles. Step 6: The scores indicate which session is differentiated by each PC. Step 7: Extraction of factor loadings, i.e. correlation between each gait variable and each PC is executed. Step 8: Variables are regrouped with the highest factor loading ($|value|>0.5$, $p<0.05$) into functional clusters (CL) PC1 and reveal that recovery of voluntary locomotion in overground-trained subject results from a strong synergy between ankle extension, trunk extension, and hip flexion, as well as improved interlimb coordination, increased weight bearing capacities, enhanced lateral foot motion, and near-normal control of hindlimb endpoint trajectory. PC2 indicates that treadmill-trained subject shows highly stable posture, but fails to initiate forward locomotion. In turn, overground-trained subject exhibits enhanced lateral body movements that alternatively load the left and right hindlimbs during locomotion, and thus help to maintain dynamic balance. PC3 highlights the flexed posture and slow hindlimb motion of the subject in the sub-acute state.

The detailed description of the invention illustrates that the combination of a multidirectional trunk support and a device for epidural electrical stimulation is essential for an apparatus for recovering voluntary control of locomotion according to the present invention.

The following examples further illustrate the invention. The exemplary embodiment of the robot can be subject to technical variations well-known to the skilled person, provided they do not depart from the teaching of the present invention, in particular the functional concepts and methods herein illustrated.

Example 1

General Methods
Animals and Animal Care

All procedures and surgery were approved by the Veterinarian Office Zurich, Switzerland. The experiments were conducted on adult female Lewis rats (~200 g body weight, Centre d'Elevage R. Janvier, France). Animals were housed individually on a 12 h light/dark cycle, with access to food and water ad libitum.

Surgical Procedures and Post-Surgical Care

All procedures have been described in detail previously (Courtine, G., et al. Transformation of nonfunctional spinal circuits into functional states after the loss of brain input. *Nat Neurosci* 12, 1333-1342 (2009); Courtine, G., et al. Recovery of supraspinal control of stepping via indirect propriospinal relay connections after spinal cord injury. *Nat Med* 14, 69-74 (2008); Musienko, P., et al. Controlling specific locomotor behaviors through multidimensional monoaminergic modulation of spinal circuitries. *J Neurosci* 31, 9264-9278 (2011)). The surgical interventions were performed under general anaesthesia and aseptic conditions. The rats underwent two surgical interventions. They first were implanted with bipolar intramuscular EMG electrodes (AS632; Cooner Wire, Chatsworth, Calif.) into selected hindlimb muscles (Courtine, G., et al. Transformation of nonfunctional spinal circuits into functional states after the loss of brain input. *Nat Neurosci* 12, 1333-1342 (2009)). For some experiments, electrodes also were secured at the midline of the spinal cord at spinal level L2 and S1 by suturing wires (same as EMG wire) over the dura mater above and below the electrode (Courtine, 2009.). The rats were allowed to recover for 2 weeks post-implantation. After completion of pre-lesion behavioral recordings, the rats underwent a second surgical intervention during which they received a SCI or a stroke. SCIs included complete transection of the thoracic (T7) spinal cord (Courtine, 2009), right cervical (C7) lateral hemisection (Courtine, 2008), or two lateral hemisections placed on opposite sides and at different spinal levels (T7 and T10) (Courtine 2008). Ischemic lesion to the cortex (stroke) was induced by injecting the vasoconstrictor endothelin-1 (ET-1, 0.3 µg·µl-1; Sigma-Aldrich) at 14 locations into the left motor cortex (fore- and hindlimb areas). We injected a volume of 500 nl at a depth of 1.2 mm with a rate of 6 $nl·s^{-1}$. After each injection, the needle was left in place for 3 min before it was carefully removed (Zörner, B., et al. Profiling locomotor recovery: comprehensive quantification of impairments after CNS damage in rodents. *Nature methods* 7, 701-708 (2010)). The extent and location of the lesions was verified post-mortem. Complete transection SCIs were inspected visually. The extent of the thoracic and cervical hemisections was measured on 40-µm thick transverse sections incubated in serum containing anti-GFAP (1:1000, Dako, USA) antibodies. We measured the extent of the lateral lesions over 5 locations equally spaced over the dorso-ventral aspect of the spinal cord. These values were expressed as a percentage of the total medio-lateral length, and averaged to obtain a unified measure of the lesion extent. Hemisection SCIs ranged from 49.8% to 54% (50.8+/−0.48%). In addition, qualitative inspections were carried out to ensure that the lesions conformed to the following specific criteria: (i) minimal sparing of the ipsilesional spinal cord defined as the absence of white matter sparing, (ii) minimal damage to the contralesional spinal cord defined as the near-complete integrity of dorsal and ventral white matter tracts.

Locomotor Tasks

A total of 7 locomotor tasks were used in the present experiments: bipedal locomotion on a moving treadmill belt (13 $cm·s^{-1}$), bipedal walking along a straight runway, quadrupedal walking along a straight runway, lateral perturbation during quadrupedal walking along a straight runway, quadrupedal walking along irregularly-spaced round rungs, quadrupedal climbing on a staircase, and quadrupedal steering along a 90 deg-curved runway. The attachment of the rat onto the back plate differed across the tasks and between the various types of injuries. For bipedal locomotion, the rats wore an upper-body jacket that extended from the back of the neck to the iliac crest. The back plate was attached over the entire extent of the jacket via a Velcro strip. For quadrupedal locomotion, the rats wore a whole-body jacket that presented two points of attachment, i.e. at the pelvis or at the mid-thoracic level. The location of the back plate attachment was selected based upon the specific gait impairment exhibited by the rat. Typically, the robot was attached to the pelvis when the rats presented alteration of hindlimb locomotor control, whereas the mid-thoracic attachment was selected when the rats showed impairment of balance.

Behavioral Training of the Rats

When the rats first wore the whole-body jacket, they displayed changes in their gait pattern. Consequently, the rats were acclimatized to wearing the custom-made jacket for 1-2 weeks while navigating freely along the runways. When no significant difference could be observed between locomotion with and without jacket (p>0.1), we trained the animals daily in 1 or 2 sessions until they crossed the runways with a constant speed. Positive reinforcement (food reward) was used to encourage the rats to perform the requested tasks. Rats were trained on the ladder with a regular arrangement of rungs. For testing, rung sequences were irregular and varied to avoid habituation to a particular rung pattern (Zörner, B., et al. Profiling locomotor recovery: comprehensive quantification of impairments after CNS damage in rodents. Nature methods 7, 701-708 (2010)).

Motor Control Enabling Factors

To facilitate locomotion in paralyzed rats, we applied epidural electrical stimulation and a cocktail of monoamine agonists (Musienko, P., et al. Controlling specific locomotor behaviors through multidimensional monoaminergic modulation of spinal circuitries. *J Neurosci* 31, 9264-9278 (2011)). Rectangular pulses (0.2 ms duration) were delivered at 40 Hz using two constant-current stimulators (AM-Systems, WA, USA) connected to the L2 and S1 electrodes. The intensity of stimulation was adjusted (50-200 µA) to obtain optimal facilitation of stepping visually. The rats also received a systemic administration of agonists to 5HT1A/7 (8-OH-DPAT, 0.05-0.1 $mg·Kg^{-1}$), 5HT2A/C (quipazine, 0.2-0.3 $mg·Kg^{-1}$), and SKF-81297 (0.15-0.2 $mg·Kg^{-1}$).

Testing Protocols 10 step cycles (treadmill) or 10 trials (runways) were typically recorded for each rat in a given experimental condition. The conditions with and without robot were randomized across rats. The rats wore the body jacket during walking with and without the robot in order to maintain the same testing conditions for both types of recordings. When using electrical and pharmacological stimulations to facilitate locomotion, stepping was recorded about 10 min after drug injection.

Neurorehabilitative Training

Rats were subjected to 30-min training sessions 6 days per week; starting 12 d post-injury. They were trained for 7 weeks. Locomotion was enabled by electrical and pharmacological stimulations. During each training session, the rats practiced quadrupedal locomotion along the horizontal straight runway, on the staircase, and along the 90 deg-curved runway. We adjusted the respective duration of each task according to the current capacities of the animals. For example, rats only performed a few runs along the curve during each training session until week 4-5, when they started showing recovery of balance control.

Kinematics, Kinetic, and EMG Recordings

Kinematics.

3-D video recordings (200 Hz) were made using a motion capture system (Vicon, Oxford, UK). 12 infrared T10 cameras were used to track the motion of reflective markers attached bilaterally at the scapula (scap), iliac crest, greater trochanter (hip), lateral condyle (knee), lateral malleolus (ankle), the distal end of the fifth metatarsal (MTP), and the tip of the toe. Nexus (Vicon, Oxford, UK) was used to obtain 3D coordinates of the markers. The body was modelled as an interconnected chain of rigid segments, and joint angles were generated accordingly. The main limb axis was defined as the virtual line connecting the greater trochanter to the lateral malleolus.

EMG.

EMG signals (2 kHz) were amplified, filtered (10-1000 Hz bandpass), stored, and analyzed off-line to compute the amplitude, duration, and timing of individual bursts (Courtine, G., et al. Transformation of nonfunctional spinal circuits into functional states after the loss of brain input. *Nat*

*Neurosci* 12, 1333-1342 (2009)). To evaluate temporal coordination between muscles, we generated probability density distributions of normalized EMG amplitudes of agonist and antagonist muscles, as described previously (Courtine, G., et al. Transformation of nonfunctional spinal circuits into functional states after the loss of brain input. *Nat Neurosci* 12, 1333-1342 (2009)).

Kinetics.

Ground reaction torques and ground reaction forces in the vertical, antero-posterior, and medio-lateral directions were monitored using a force-plate (2 kHz, HE6X6, AMTI, USA) located below the treadmill belt or in the middle of the runway.

Data Analysis

A minimum of 10 step cycles was extracted for both the left and right hindlimbs for each experimental condition and rat. A total of 148 parameters quantifying gait, kinematics, kinetics, and EMG features were computed for each limb and gait cycle according to methods described in detail previously (Courtine, G., et al. Transformation of nonfunctional spinal circuits into functional states after the loss of brain input. *Nat Neurosci* 12, 1333-1342 (2009), Courtine, G., et al. Recovery of supraspinal control of stepping via indirect propriospinal relay connections after spinal cord injury. *Nat Med* 14, 69-74 (2008), Musienko, P., et al. Controlling specific locomotor behaviors through multidimensional monoaminergic modulation of spinal circuitries. *J Neurosci* 31, 9264-9278 (2011)). These parameters provide a holistic quantification of locomotor patterns ranging from general features of gait and performance to fine details of limb motions.

Statistical Analyses

The various experimental conditions were associated with substantial modulation of gait patterns, which were evident in the modifications of a large proportion of the computed parameters. In order to evaluate the more important and reproducible modulation patterns mediated by the different conditions as well as the correlations between the modulated parameters, we implemented a multi-step statistical procedure based on principal component (PC) analysis (Courtine, G., et al. Transformation of nonfunctional spinal circuits into functional states after the loss of brain input. *Nat Neurosci* 12, 1333-1342 (2009)). PC analyses were applied on data from all individual gait cycles for all the rats together. Data were analyzed using the correlation method, which adjusts the mean of the data to zero and the standard deviation to 1. This is a conservative procedure that is appropriate for variables that differ in their variance (e.g. kinematic vs. EMG data).

All data are treated as mean values±S.E.M. Repeated-measures ANOVAs and Student's paired t-tests were used to test differences between normally distributed data (Kolmogorov-Smirnov test) from the various experimental conditions. Non-parametric tests (Wilcoxon and Kruskall Wallis) were used instead when the distribution was not normal.

Robotic Interface

A robotic system to provide rats with adjustable trunk support along 4 independent degrees of freedom (DoF) was built. Three actuated linear modules CKK 20-145, CKK 15-110 and CKK 12-90, Bosch Rexroth AG, distributor: Amsler AG, Feuerthalen, Switzerland, are arranged defining a large Cartesian workspace capable of translating the rat in x, y, z directions. The first two axes (see for reference FIG. 1, x and y), which are used for movements in the horizontal plane, cover an area of 1.2 m². The third axis (see for reference FIG. 1, z) provides the rat with support against gravity, and allows vertical movements over a range of 35 cm. At the extremity of this Cartesian structure, a fourth motor (RE25, Maxon motor AG, Sachseln, Switzerland) actuates rotations (300 deg) about the vertical axis (see for reference FIG. 1, φ). This serial configuration provides a large workspace in which forces can be applied to the rat while preventing inclinations about the horizontal directions.

In order to let the robotic system behave transparently, i.e. allowing the rats to walk freely in the entire workspace without "feeling" the robot, the interaction forces between the subject and the robot have to be reduced to a minimum. The inertia of the robot (106 kg in x direction, 32 kg in y direction, 29 kg in z direction) is significantly larger than the mass of the rat (<0.25 kg).

A lightweight, low-friction (<10 g), compliant module consisting of a base platform with three protruding legs forming a cage, a spring-suspended platform within this cage, and a Delta structure that constrains the unactuated DoF (i.e. tilting of the rat) is provided (see for reference FIG. 2). The suspended platform is connected to the cage via six linear springs (angle in the horizontal plane, 120 deg angle; stiffness, 112 N/m for upper springs, 57 N/m for lower springs, (see for reference FIG. 2). An additional spring pair is attached to the rotating shaft in the center of the suspended platform, providing the elastic decoupling about the vertical axis. Together, this configuration decouples the inertia of the serial module from the suspension platform in the 4 actuated DoFs.

The Delta structure allows measurement of the displacements of the suspended platform, and thereby the deflection of the springs along each DoF, providing an inexpensive way of measuring interaction forces or torques. Four contact-free magnetic encoders (12-bit, Austria microsystems, Austria) are located in the joints of the Delta structure. The position of the end-effector with respect to the serial robot is calculated by combining information from these angular sensors and a forward kinematic model of the Delta structure. The relative position of the platform encodes the spring lengths, and thereby the interaction forces and torques that are derived from the linear spring characteristics.

These forces and torques are used in the force control loop of the robot (see for reference FIG. 4). The control strategy is implemented in MATLAB/Simulink and executed in real-time on a desktop computer running xPC target (Sampling rate, 1 kHz). This computer communicates with the motor drives and acquires information coming from the sensors. It also exchanges information with a second computer that runs a user interface for online changes of the control parameters for the robot.

The SEA-based elastic decoupling allows to set extremely high control gains without affecting stability. The resulting reflected mass of the stiff robot is: 787 g in x direction, 104 g in y direction, 22 g in z direction, and 998 g·cm$^{-2}$ in rotation direction. Due to the use of the multidimensional SEA, this inertia only dominates the perceived dynamics for low-frequent excitations, for which inertial forces are low. For high-frequent excitations, which are generally associated with reduced amplitudes of motion, the physical properties of the springs dominate the response, also leading to low forces. Consequently, the rat mainly feels the inertia of the suspended platform, which is 109.1 g. The bandwidth of the SEA system is ~2.5 Hz in x direction, ~2.8 Hz in y direction, ~13 Hz in z direction, ~2.2 Hz in rotation.

To demonstrate the transparency of the robot, we compared the kinematics and muscle activity underlying locomotion of healthy rats (n=7) walking along a straight runway with and without the robot. The results were evaluated through stick diagram decomposition of hindlimb motion during stance and swing together with limb endpoint trajectory, hindlimb joint angles, and EMG activity of medial gastrocnemius (MG) and tibialis anterior (TA) muscles during locomotion along a straight runway without and with robotic support. Despite detailed analyses, we did not detect significant differences between these conditions ($p>0.3$, FIG. 3A, panel A), indicating that the massive robot did not interfere with gait. We confirmed these results during walking on a horizontal ladder ($n=5$). Even in such challenging conditions, precise paw placement ($p>0.4$) and gait features were virtually unaffected by the robotic interface ($p>0.3$, FIG. 3A, panel B).

Evaluation Mode

The purpose of this test is to compare the effect of the prior art spring-like vs. constant-force BWS conditions on locomotor pattern generation in rats with complete SCI ($n=5$,). Rats received a complete SCI that led to permanent hindlimb paralysis.

To enable stepping, we applied a combination of epidural electrical stimulation and monoamine agonists (Courtine, G., et al. Transformation of nonfunctional spinal circuits into functional states after the loss of brain input. *Nat Neurosci* 12, 1333-1342 (2009)). We evaluated the performance by elaborating stick diagram decomposition of hindlimb motion with spring-like vs. constant-force BWS together with successive limb endpoint trajectories ($n=10$ steps), activity of TA and MG muscles, and vertical ground reaction forces. We tuned the spring-constant to an optimal value for facilitating stepping (Courtine, G., et al. Transformation of nonfunctional spinal circuits into functional states after the loss of brain input. *Nat Neurosci* 12, 1333-1342 (2009)), and maintained the exact same amount of support during constant-force conditions. Compared to spring-like BWS, the constant-force BWS markedly improved the quality and consistency ($p<0.01$) of gait features, and promoted locomotor patterns that converged towards those of healthy rats ($p<0.01$, see FIG. 3A, panel C).

The human (Harkema, S., et al. Effect of epidural stimulation of the lumbosacral spinal cord on voluntary movement, standing, and assisted stepping after motor complete paraplegia: a case study. *Lancet* 377, 1938-1947 (2011)) and rat (Courtine, G., et al. Transformation of nonfunctional spinal circuits into functional states after the loss of brain input. *Nat Neurosci* 12, 1333-1342 (2009), Timoszyk, W. K., et al. Hindlimb loading determines stepping quantity and quality following spinal cord transection. *Brain Res* 1050, 180-189 (2005)) lumbosacral spinal cord can interpret weight-bearing information during stepping. We evaluated whether weight-bearing input also determines gait quality in rats with complete SCI ($n=4$). Decreasing the level of BWS resulted in graded adjustments in hindlimb kinematics, forces, and muscle activity ($p<0.01$), which confirmed the ability of lumbosacral circuitries to transform weight-bearing information into specific locomotor patterns. However, we found an inverted U-shaped relationship ($R^2=0.87$) between gait quality and the level of BWS.

These findings demonstrate that an optimal constant-force support conditions are useful for enabling and training locomotion in subjects with gait disorders.

A unilateral cortical stroke has limited impact on basic locomotion in rats, but behavioral observations have suggested deficits in balance control (Zörner, B., et al. Profiling locomotor recovery: comprehensive quantification of impairments after CNS damage in rodents. *Nature methods* 7, 701-708 (2010)). To demonstrate impairment of equilibrium after stroke, we exploited the capacity of the robot to superimpose any force at any time and in any actuated DoF onto the transparent control mode. Specifically, we applied a sudden triangular-shaped force (2.5N, 1 s rightward during runway locomotion in rats with a left-sided cortical stroke) in the medio-lateral direction (y axis, pushing rightward) for is while rats were progressing freely along a straight runway. Shortly after a left-sided stroke (6d), the rats failed to compensate for the perturbation. They displayed ample rightward deviations ($p<0.002$, averaged ($n=5$ rats) lateral trunk displacements 1 s before, during, and 2 s after perturbation) and frequently fell off the runway (56±39%, mean±S.D.). After one month of recovery, the rats responded to the perturbation with a controlled co-activation of extensor and flexor muscles, followed by a prolonged activity of contralesional extensor muscles (360+/−80%, $p<0.001$). This muscle synergy stabilized the trunk and hindlimb, and produced substantial mediolateral forces ($p<0.001$, 0.60±0.07N at 6d vs. 1.54±0.18N at 30$d$ post-lesion) that restored the locomotor trajectory.

Collectively, these results demonstrate that the evaluation mode of the robotic interface provides heuristic conditions to assess motor pattern generation and balance following neuromotor impairments.

Enabling Mode

We next sought to utilize the robotic interface as a propulsive or postural neuroprosthesis that provides adjustable assistance to propel the body forward and to restore postural orientation and stability. We showed that this so-called enabling mode would uncover unexpected locomotor capacities that are dissimulated by impairments in propulsion and/or balance.

Electrical and pharmacological stimulations enable locomotion in rats with complete SCI, but the animals fail to produce the necessary forces to propel their body forward overground. Instead, they display tonic activity in extensor muscles, behaviorally apparent as standing. To compensate for the lack of propulsion, we configured the robot to act as a propulsive neuroprosthesis that moved the rats forward (x axis, 13 cm. $s^{-1}$) while providing constant-force vertical support (60+/−10% of BWS). When initiating the robotic sequence, the rats smoothly transitioned from quiet standing to continuous locomotion. Rhythmic movements arrested instantly when the propulsive neuroprosthesis stopped translating the rat forward.

Rats with unilateral cortical stroke display significant impairments in contralesional paw placement when crossing a horizontal ladder (Zörner, B., et al. Profiling locomotor recovery: comprehensive quantification of impairments after CNS damage in rodents. *Nature methods* 7, 701-708 (2010)). These deficits have been attributed to the loss of visuomotor control, which heavily relies on the damaged motor cortex (Drew, T., Andujar, J. E., Lajoie, K. & Yakovenko, S. Cortical mechanisms involved in visuomotor coordination during precision walking. *Brain Res Rev* 57, 199-211 (2008)). We tested the hypothesis that impaired equilibrium maintenance may also contribute to the alteration of skilled locomotion after a cortical stroke. We configured the robotic interface to act as a postural neuroprosthesis. In this enabling mode, the robot provided a constant-force support in the vertical direction (z axis, 27±4% of BWS) and stiff support in the lateral directions (y and rotational axes). The robotic postural neuroprosthesis instantly improved the rats' ability to position their contralesional hindpaw accurately onto the irregularly spaced rungs of the ladder ($p<0.002$,). Statistical analyses showed that the robot significantly decreased the number of miss/slip ($p<0.01$, FIG. 34, panel D), which correlated with improved postural stability ($p<0.01$,).

We next assessed the capacity of the robotic postural neuroprosthesis to enable motor control in rats with a lateral C7 hemisection (n=5). Stick diagram decomposition of hindlimb motion during climbing on a staircase pre-lesion, showing hindlimb oscillations and EMG activity of MG and TA muscles were recorded. PC analysis was applied on all gaits and rats. Ten days post-lesion, the rats dragged the ipsilesional hindlimb during locomotion, especially during climbing on a staircase without and with constant-force robotic support. Without robotic support, they stumbled against, and rarely stepped onto the staircase. The robotic postural neuroprosthesis instantly enabled coordinated plantar stepping, both during horizontal walking (32±4% of BWS;) and climbing on a staircase (28±3% of PWS;). The robotic support restored trunk orientation and stability ($p<0.001$), which correlated with near-normal hindlimb kinematics and accurate positioning of the ipsilesional paw onto the staircase ($p<0.001$, FIG. 3B, panel E, left).

We then investigated whether the robotic postural neuroprosthesis could enable motor control shortly after a more severe SCI consisting of two lateral hemisections placed on opposite sides and at different spinal levels (T7 and T10). This SCI completely interrupted direct supraspinal input, thus leading to permanent hindlimb paralysis (E. S. Rosenzweig et al., Extensive spontaneous plasticity of corticospinal projections after primate spinal cord injury. *Nat Neurosci* 13, 1505 (December, 2010)). To enable locomotion as early as 12 days post-SCI, we applied electrical and pharmacological stimulations. Animals were tested for locomotion on a staircase without and with constant-force robotic support 12d after staggered hemisections. Locomotion was tested without (spontaneous) and with electrical and pharmacological stimulations. Without robotic support, the rats exhibited rhythmic hindlimb movements, but they failed to perform plantar steps (91±7% of dragging) and often fell laterally during walking. With the robotic postural neuroprosthesis, all the tested rats (n=5) displayed bilateral weight-bearing plantar steps. Despite the interruption of direct supraspinal pathways, the rats immediately regained the ability to accurately position both hindpaws onto the staircase ($p<0.001$). The otherwise paralyzed rats demonstrated gait patterns that were nearly indistinguishable from those of healthy rats, both during horizontal locomotion and stair climbing (FIG. 3B, panel E, right). For both tasks, improvement of hindlimb locomotion correlated with robot-enabled recovery of trunk position and stability.

Together, these findings demonstrate that the enabling mode of the robotic interface instantly restored unexpected locomotor capacities across a wide range of natural walking behaviors after moderate to severe neuromotor impairments.

Training Mode

Finally, we exploited the enabling mode of the robotic interface to enhance functional capacities with repeated practice; a control scheme that we termed training mode. We subjected rats (n=6) with staggered hemisection SCIs to 30-min locomotor training sessions every other day for 8 weeks (see Methods). Rats were positioned quadrupedally in the robotic interface, which provided constant-force vertical support against gravity (z axis) but was set transparent in the other directions (x, y, and $\varphi$ axes). The rats walked along a 90 deg-curved runway. Trunk orientation was measured as the angle between the pelvis and the orientation of the upper body velocity vector, termed heading, which also defined the locomotor trajectory. Locomotion was enabled by electrical and pharmacological stimulations. At 9 weeks post-lesion, non-trained rats displayed weight-bearing steps, but they failed to control body inertia and balance during robot-assisted locomotion along a curved runway ($p<0.001$, FIG. 3B, panel F, left)). In contrast, trained rats were capable of steering curves (FIG. 3B, panel F, right) while maintaining equilibrated trunk movements ($p<0.001$).

These results reveal that the training mode of the robotic interface significantly improved locomotor capacities in rats with paralyzing SCI.

Example 2

Materials and Methods
Animals and Behavioral Training

Experiments were conducted on adult female Lewis rats (200-220 g body weight) housed individually on a 12-hour light/dark cycle with access to food and water ad libitum. All experimental procedures were approved by the Veterinary Office of the Canton of Zurich. Prior to surgery, all the rats (non-trained and trained) were first acclimatized to wearing the custom-made jacket for 1-2 weeks while navigating freely along the runway. The rats were then trained for an additional 1-2 weeks to walk bipedally. All the rats learned this task rapidly. Typically, they produced consistent stepping patterns within 1-2 sessions. Positive reinforcement (food reward) was used to encourage the rats to perform the requested tasks.

Surgical Procedures

All basic surgical procedures and post-operative care for SCI rats have been described in detail previously (R. G. Lovely, R. J. Gregor, R. R. Roy, V. R. Edgerton, Effects of training on the recovery of full-weight-bearing stepping in the adult spinal cat. *Experimental neurology* 92, 421 (May, 1986); A. Wernig, S. Muller, Laufband locomotion with body weight support improved walking in persons with severe spinal cord injuries. *Paraplegia* 30, 229 (April, 1992); S. Harkema et al., Effect of epidural stimulation of the lumbosacral spinal cord on voluntary movement, standing, and assisted stepping after motor complete paraplegia: a case study. *Lancet* 377, 1938 (Jun. 4, 2011)). Briefly, under general anaesthesia and aseptic conditions, bipolar EMG electrodes were inserted into hindlimb muscles. Two stimulating electrodes were secured onto the dura at the midline of spinal levels L2 and S1. After pre-lesion recordings, rats received a left T7 lateral over-hemisection and a right lateral hemisection at T10 (Courtine et al. Recovery of supraspinal control of stepping via indirect propriospinal relay connections after spinal cord injury, *Nature Medicine* 2008). For the T7 over-hemisection, we aimed at interrupting the dorsal column bilaterally while sparing ventral pathways on the contralateral side. The completeness of the hemisections was assessed on 30-µm thick longitudinal sections incubated in serum containing anti-GFAP (1:1000, Dako, USA) antibodies. In addition, we confirmed the absence of BDA-labeled corticospinal axons in the dorsal column of the T8 spinal segment in transverse sections.

Multi-System Neuroprosthetic Training

Ten min prior to training, the rats received a systemic (I.P.) administration of quipazine (5-HT2A/C, 0.2-0.3 mg/kg), SKF-82197 (D1, 0.1-0.2 mg/kg) and 8-OH-DPAT (5-HT1A/7, 0.05-0.2 mg/kg). During training, we delivered monopolar electrical stimulation (0.2 ms, 100-300 µA, 40 Hz) through L2 and S1 electrodes. Locomotor training was conducted bipedally on a treadmill (9 cm/s) with vertical robotic support, as well as overground with a robotic postural interface. The content of each training session evolved with the actual capacities of the rats and training objectives. Positive reinforcement was used to encourage the rats to perform the requested tasks. An additional group of rats was trained with the same frequency and duration, but rehabilitation was restricted to step training on a treadmill. These rats were trained to walk bipedally overground with the robotic postural interface for 2 weeks prior to the lesion. They were also tested in this paradigm at 1 and 9 weeks post-lesion. At the end of the training period, treadmill-trained rats practiced overground locomotion with the robotic postural interface for about 10 min per day during 4-8 sessions to ensure that the specificity of the task was not responsible for their incapacity to initiate and sustain locomotion.

Kinematic, Kinetic and EMG Recordings and Analysis

Bipedal locomotion was recorded on a treadmill (9 cm/s) as well as overground. Kinematic (12 cameras, 200 Hz), kinetic (force plate, 2 kHz) and EMG (2 kHz, 10-1000 Hz bandpass) recordings were performed using an integrated motion capture system. Procedures for data collection, data analysis, and computation have been described in detail previously (Courtine et al. Transformation of nonfunctional spinal circuits into functional states after the loss of brain input *Nature Neuroscience* 2009). To quantify locomotor performance, we applied a principal component (PC) analysis on all the computed variables (Courtine et al. Transformation of nonfunctional spinal circuits into functional states after the loss of brain input *Nature Neuroscience* 2009) provides a step-by-step explanation of the procedure and interpretation. We quantified recovery of locomotor function as the distance between gait cycles of intact and injured rats in the 3D space created by PC1-3 (M. Hagglund, L. Borgius, K. J. Dougherty, O. Kiehn, Activation of groups of excitatory neurons in the mammalian spinal cord or hindbrain evokes locomotion. *Nat Neurosci* 13, 246 (February, 2010)).

Brain Stimulation and Recordings

A monopolar electrode was implanted epidurally over the left hindlimb motor cortex. A train of stimuli (0.2 ms, 10 ms pulse length, 300 Hz, 0.5-1.5 mA) was delivered during bipedal standing in fully awake conditions. Testing was performed without and with electrochemical stimulations. Peak-to-peak amplitude and latency of evoked responses were computed from EMG recordings of the left TA muscle.

Neuronal Modulations

At 60-70 days post-injury, a microwire array (16 or 32 channel) was implanted stereotaxically into layer V of the hindlimb area of the left motor cortex. Recordings were conducted 5-7 days post-surgery. Neural signals were acquired (24.4 kHz) with a neurophysiology workstation synchronized to kinematic recordings. All spike-sorting was performed offline via super-paramagnetic clustering (J. Liu, L. M. Jordan, Stimulation of the parapyramidal region of the neonatal rat brain stem produces locomotor-like activity involving spinal 5-HT7 and 5-HT2A receptors. *Journal of neurophysiology* 94, 1392 (August, 2005)). Clusters were manually tuned based on established principles (G. Courtine et al., Can experiments in nonhuman primates expedite the translation of treatments for spinal cord injury in humans? *Nature medicine* 13, 561 (May, 2007)) to identify single units. Modulations were analyzed in single experimental sessions to avoid potential instability confounds. Two recurring behaviors were used to evaluate the significance of neuronal modulations. (i) Initiation was defined as swing onset from rest. (ii) Correction was defined as beginning of swing phase after irregular gait. A two-sample Kolmogorov-Smirnov test compared firing rates (estimated in 250 ms windows) in successive, one-second periods encompassing initiation and correction to determine whether modulations were significant.

NMDA and Muscimol Microinjections

To ablate T8-T9 neurons, we infused NMDA (1% in $dH_2O$) into 14 sites (depth 1 mm, total volume 3 µl) covering spinal levels T8-T9. Rats were tested 5 days post-lesion, and sacrificed on the following day. The ablation of neurons was verified post mortem on tissue sections stained with mouse anti-NeuN (1:500, Chemicon, USA) antibodies. To inactivate the motor cortex, we injected the GABA-agonist muscimol intra-cortically (800 nl, 4.5 mg/Kg). Five days prior to experiments, we stereotaxically implanted a catheter (OD: 0.61 mm, ID: 0.28 mm) into the left motor cortex at a depth of 1.5 mm. Proper catheter location was verified post mortem on tissue sections stained (Invitrogen, USA) for fluorescent Nissl visualization.

Tracing and Immunohistochemistry

We conducted retrograde tract tracing by infusing Fast-blue (2% in 0.1M phosphate buffer and 2% dimethyl sulfoxide) bilaterally into L1-L2 spinal segments (Courtine et al. Recovery of supraspinal control of stepping via indirect propriospinal relay connections after spinal cord injury, *Nature Medicine* 2008). A total of 1.2 µl was pressure-injected over 6 sites (depth 1.5 mm). To trace motor cortex axonal projections, we injected the anterograde tracer BDA 10,000 (10% in 0.01M PBS) into the left motor cortex over 6 sites covering the hindlimb area (coordinates centered −1 mm rostrocaudal and −1.75 mm mediolateral to Bregma, depth 1.5 mm). The rats were perfused 18 days later with Ringer's solution containing 100,000 IU/L heparin and 0.25% $NaNO_2$ followed by 4% phosphate buffered paraformaldehyde, pH 7.4 containing 5% sucrose. For cfos experiments, rats were perfused 60 min after cessation of a 45 min bout of continuous locomotion (R. G. Lovely, R. J. Gregor, R. R. Roy, V. R. Edgerton, Effects of training on the recovery of full-weight-bearing stepping in the adult spinal cat. *Experimental neurology* 92, 421 (May, 1986)). Locomotion was performed overground for intact and overground-trained rats, and during overground guided locomotion for treadmill-trained and non-trained rats in order to ensure the presence of stepping in all the animals. The brain, brainstem, and spinal cords were dissected, post-fixed overnight, and transferred to 30% phosphate buffered sucrose for cryoprotection. After 4 days, the tissue was embedded and sectioned on a cryostat at a 40-µm thickness.

For immunohistochemistry experiments, sections were incubated in serum containing rabbit anti-cfos (1:2000, Santa Cruz Biotechnologies, USA), anti-GFAP (1:1000, Dako, USA), or anti-5HT (1:5000, Sigma Aldrich, Germany), or mouse anti-synaptophysin (1:1000, Millipore, USA) antibodies. Immunoreactions were visualized with secondary antibodies labeled with Alexa Fluor® 488 or 555. BDA-labeled fibers were detected using streptavidin-horseradish peroxidase (1:200) in 0.1M PBS-Triton (1%). Tyramide signal amplification Cyanine 3 was used at a dilution of 1:100 for 1 min.

Neuromorphological Evaluations

Fastblue- and cfos-positive neurons were counted using image analysis software on 5 evenly spaced slices separated by 1.2 mm and centered on the T8-T9 junction. Fiber density was measured using 5 confocal image stacks per region per rat acquired with standard imaging settings and analyzed using custom-written scripts according to previously described methods (L. T. Alto et al., Chemotropic guidance facilitates axonal regeneration and synapse formation after spinal cord injury. *Nat Neurosci* 12, 1106 (September, 2009)). Confocal output images were divided into square regions of interest (ROI), and densities computed within each ROI as the ratio of traced fibers (amount of pixels) per ROI area. Files were color-filtered and binarized by means of an intensity threshold. Threshold values were set empirically and maintained across sections, animals and groups. Comparisons of computerized and manual counting of CST labeling in T8-T9 showed no differences between both methods. Manual fiber counts were conducted on spinal cord sections overlaid with 5 vertical lines. Fibers crossing these lines within the grey matter were marked, and all intersecting fibers on 3 sections per rat were summed to obtain a cumulative count. Both manual and computerized counts were performed blindly. Image acquisition was performed using a laser confocal scanning microscope and the LAS AF interface and stacks were processed offline.

Statistics

All data are reported as mean values±s.e.m. Statistical evaluations were performed using one- or two-way ANOVA, repeated-measures ANOVA, or non-parametric Wilcoxon tests. The post hoc Kruskall-Wallis test was applied when appropriate. Adult rats received a left lateral over-hemisection at T7 and a right lateral hemisection at T10. This SCI interrupts all direct supraspinal pathways, but leaves an intervening gap of intact tissue. The lesion, however, led to a complete loss of hindlimb function, with no sign of recovery over 2 months post-injury. Likewise, humans with clinically complete SCI frequently show maintenance of connections through the lesion (B. A. Kakulas, A review of the neuropathology of human spinal cord injury with emphasis on special features. *J Spinal Cord Med* 22, 119 (Summer, 1999)). Thus, this experimental lesion reproduces key anatomical and functional features of human SCIs, while providing well-controlled conditions to investigate the mechanisms underlying recovery (G. Courtine et al., Recovery of supraspinal control of stepping via indirect propriospinal relay connections after spinal cord injury. *Nature medicine* 14, 69 (January, 2008)).

To transform lumbosacral circuits from dormant to highly functional states (P. Musienko, J. Heutschi, L. Friedli, R. V. den Brand, G. Courtine, Multi-system neurorehabilitative strategies to restore motor functions following severe spinal cord injury. *Experimental neurology,* (Sep. 7, 2011)), we applied tonic (40 Hz) epidural electrical stimulation over L2 and S1 spinal segments (G. Courtine et al., Transformation of nonfunctional spinal circuits into functional states after the loss of brain input. *Nat Neurosci* 12, 1333 (October, 2009), and systemically administered a tailored cocktail of $5HT_{1A/7}$, $5HT_{2A/C}$, and $D_1$ receptor agonists (P. Musienko et al., Controlling specific locomotor behaviors through multidimensional monoaminergic modulation of spinal circuitries. *J Neurosci* 31, 9264 (Jun. 22, 2011)). By increasing the general level of spinal excitability, this electrochemical spinal neuroprosthesis enables sensory information to become a source of control for stepping (G. Courtine et al., Transformation of nonfunctional spinal circuits into functional states after the loss of brain input. *Nat Neurosci* 12, 1333 (October, 2009), P. Musienko, J. Heutschi, L. Friedli, R. V. den Brand, G. Courtine, Multi-system neurorehabilitative strategies to restore motor functions following severe spinal cord injury. *Experimental neurology,* (Sep. 7, 2011)). This intervention promoted coordinated, although involuntary, bipedal stepping on a treadmill as early as 7 days post-injury.

These stepping movements are elicited by the moving treadmill belt (G. Courtine et al., Transformation of nonfunctional spinal circuits into functional states after the loss of brain input. *Nat Neurosci* 12, 1333 (October, 2009)), suggesting that the rats would not be capable of voluntarily initiating hindlimb locomotion overground. To verify the absence of supraspinal control, we applied the electrochemical neuroprosthesis, and positioned the same rats bipedally in a robotic postural interface that provided adjustable vertical and lateral trunk support, but did not facilitate locomotion in any direction. All the rats (n=27) failed to initiate hindlimb locomotion overground at 7 days post-injury (p<0.001).

We then designed a multi-system neuroprosthetic training program that encompassed two objectives. First, we aimed to improve the functionality of lumbosacral circuits through treadmill-based training enabled by the electrochemical neuroprosthesis (G. Courtine et al., Transformation of nonfunctional spinal circuits into functional states after the loss of brain input. *Nat Neurosci* 12, 1333 (October, 2009)). Second, we sought to promote the recovery of supraspinally-mediated movements; we exploited the robotic postural interface not only to enable, but also to force the rats to actively use their paralyzed hindlimbs in order to locomote bipedally towards a target.

Rats (n=10) were trained daily for 30 min with a combination of both paradigms, starting 7-8 days post-injury). The first, effortful voluntary steps emerged after 2-3 weeks of training (p<0.01). As voluntary movements recovered, we gradually increased the relative duration of overground training. 5-6 weeks post-injury, all the rats were capable of initiating and sustaining full weight-bearing bipedal locomotion for extended periods of time, but only during electrochemically enabled motor states. Kinematic analyses revealed that overground-trained rats deployed a similar control strategy as intact animals to produce locomotion. To measure recovery, we adapted the clinically standardized 6-minute walk test (G. H. Guyatt et al., The 6-minute walk: a new measure of exercise capacity in patients with chronic heart failure. *Can Med Assoc J* 132, 919 (Apr. 15, 1985)) to bipedally stepping rats. Overground-trained animals with a paralyzing SCI covered distances as long as 21 m in 3 min.

We next tested whether treadmill-restricted step training under electrochemically-enabled states would also promote the recovery of voluntary locomotion (n=7 rats). This automated step training failed to re-establish overground locomotion despite repeated testing during 4-8 sessions at 9 weeks post-injury (p<0.001. Moreover, treadmill-trained rats were not capable of sustaining robotically initiated locomotion overground.

To further enhance supraspinal contribution, we introduced stairs and obstacles; two conditions requiring voluntarily mediated gait tuning (T. Drew, J. E. Andujar, K. Lajoie, S. Yakovenko, Cortical mechanisms involved in visuomotor coordination during precision walking. *Brain Res Rev* 57, 199 (January, 2008)). After 2-3 additional weeks, overground-trained rats (previously submitted to at least 10 min treadmill to warm up before the robot training) were capable of bipedally sprinting up stairs and avoiding obstacles. To accomplish these paradigms, the animals displayed a range of task-specific adjustments of hindlimb movements.

Anatomical examinations highlighted an extensive remodelling of supraspinal and intraspinal projections in rats that regained voluntary locomotion. We first conducted retrograde tract tracing from L1-L2 locomotor centers. We found a significant increase (p<0.01) in the number of labeled neurons in intermediate and ventral laminae of T8-T9 segments in both overground-trained and treadmill-trained rats compared to non-trained animals. Analysis of the activity-dependent marker cfos after continuous overground locomotion confirmed that the labeled neurons were active during walking. The number of cfos$^{on}$ nuclei in the regions rich in neurons retrogradely labeled from L1-L2 locomotor centers was larger in overground-trained rats compared to all the other groups (p<0.05). Thoracic neurons may thus play a pivotal role in restoring voluntary locomotion (G. Courtine et al., Recovery of supraspinal control of stepping via indirect propriospinal relay connections after spinal cord injury. *Nature medicine* 14, 69 (January, 2008); F. M. Bareyre et al., The injured spinal cord spontaneously forms a new intraspinal circuit in adult rats. *Nat Neurosci* 7, 269 (March, 2004); K. C. Cowley, E. Zaporozhets, B. J. Schmidt, Propriospinal neurons are sufficient for bulbospinal transmission of the locomotor command signal in the neonatal rat spinal cord. *The Journal of physiology* 586, 1623 (Mar. 15, 2008)). To address this hypothesis, we ablated T8-T9 neurons by infusing the axon-sparing excitotoxin N-methyl-D-aspartic acid (NMDA) (G. Courtine et al., Recovery of supraspinal control of stepping via indirect propriospinal relay connections after spinal cord injury. *Nature medicine* 14, 69 (January, 2008)). Infusion of NMDA abolished the regained voluntary locomotion (p<0.01), despite uncompromised functionality of lumbosacral circuits. Likewise, overground-trained rats lost voluntary control of locomotion after the complete interruption of supraspinal input to T8-T9 neurons (p<0.01).

We labeled projections from the left hindlimb motor cortex with injections of biotinylated dextran amine (BDA)). The bilateral interruption of the dorsal column at the T7 over-hemisection only spared a few (1-2%) (C. Brosamle, M. E. Schwab, Cells of origin, course, and termination patterns of the ventral, uncrossed component of the mature rat corticospinal tract. *J Comp Neurol* 386, 293 (Sep. 22, 1997)) corticospinal tract (CST) axons in the right dorsolateral funiculus. Consequently, non-trained rats showed scarce CST labeling in T8-T9 segments. Treadmill-restricted training did not promote significant changes in the density of thoracic CST projections. In contrast, we found a reconstitution of 45±7% of pre-lesion bilateral fiber density in overground-trained rats. These CST axons exclusively branched from the right dorsolateral funiculus, and profusely innervated the right, and more unexpectedly, the left gray matter of T8-T9 segments (E. S. Rosenzweig et al., Extensive spontaneous plasticity of corticospinal projections after primate spinal cord injury. *Nat Neurosci* 13, 1505 (December, 2010)). We detected multiple CST fibers extending from the gray matter at the T7 lesion site into the right dorsolateral funiculus. These ectopic fibers, suggestive of regenerative sprouting (O. Steward, B. Zheng, M. Tessier-Lavigne, False resurrections: distinguishing regenerated from spared axons in the injured central nervous system. *J Comp Neurol* 459, 1 (Apr. 21, 2003)), led to a near two-fold increase in the CST axon density of the T8-T9 dorsolateral funiculus (p<0.001. Thoracic CST fibers bypassed the T7 over-hemisection through the right dorsolateral funiculus, branched into the gray matter, and re-crossed the midline. These fibers developed large axonal structures with bouton-like swellings suggestive of sprouting in terminal arbors. Confocal microscopy confirmed that thoracic CST fibers bore synaptic elements because they co-localized with synaptophysin. These fibers established contacts with relay neurons retrogradely labeled from L1-L2 locomotor centers.

Remodelling of motor cortex axonal projections was not restricted to the spared tissue bridge. Quantification of CST fibers at T4-T5, above the injury, revealed a significant bilateral increase of axon density in overground-trained compared to non-trained, treadmill-trained, and intact rats (p<0.01). We found a near fourfold increase in the density of cortical projections in various brainstem motor areas including the left and right vestibular nuclei (p<0.01), the entire reticular formation (p<0.001), and parapyramidal regions (p<0.01). These areas contain reticulospinal neurons and spinally projecting serotonergic (5HT) neurons that both contribute to initiating and sustaining locomotion (M. Hagglund, L. Borgius, K. J. Dougherty, O. Kiehn, Activation of groups of excitatory neurons in the mammalian spinal cord or hindbrain evokes locomotion. *Nat Neurosci* 13, 246 (February, 2010); J. Liu, L. M. Jordan, Stimulation of the parapyramidal region of the neonatal rat brain stem produces locomotor-like activity involving spinal 5-HT7 and 5-HT2A receptors. *Journal of neurophysiology* 94, 1392 (August, 2005)). Descending 5HT fibers might thus reorganize with training. We found a nearly complete, lamina-specific restoration of T8-T9 serotonergic innervation in overground-trained rats, which contrasted with the depletion of 5HT fibers in non-trained and treadmill-trained animals (p<0.05).

Collectively, these analyses demonstrate that automated treadmill-restricted training failed to mediate anatomical changes in descending pathways, whereas active training under highly functional states promoted multi-level plasticity in cortex- and brainstem-derived axonal systems.

Contrary to primates, the rodent motor cortex is not essential to produce locomotion (G. Courtine et al., Can experiments in nonhuman primates expedite the translation of treatments for spinal cord injury in humans? *Nature medicine* 13, 561 (May, 2007)). Consequently, we sought to demonstrate that training-induced remodelling of motor cortex projections did contribute to controlling voluntary locomotion. First, we implanted stimulating epidural electrodes over the left motor cortex to verify that the reorganization of neuronal pathways re-established connectivity across the lesion. Before the SCI, applying a train of low intensity (0.7-1.5 mA) electrical stimuli evoked large responses in the left tibialis anterior muscle. The SCI permanently abolished these responses in non-trained rats (p<0.001). In contrast, overground-trained rats regained responses below the lesion, averaging about 10% of their pre-lesion amplitude (p<0.001;). These responses were delayed by 12±3 ms (p<0.01), suggesting that a larger number of synaptic relays was necessary to convey the supraspinal volley to hindlimb motor pools. The amplitude of responses substantially increased during electrochemically enabled motor states (p<0.01), indicating enhanced transmission of the supraspinal command (K. C. Cowley, E. Zaporozhets, B. J. Schmidt, Propriospinal neurons are sufficient for bulbospinal transmission of the locomotor command signal in the neonatal rat spinal cord. *The Journal of physiology* 586, 1623 (Mar. 15, 2008)). Second, we implanted a microwire array in the vicinity of CST neurons projecting to T8-T9 segments, and recorded neuronal modulations during voluntary locomotion in overground-trained rats (n=3). We found a variety of neurons (n=17/24 neurons) whose modulation patterns significantly (p<0.05) correlated with gait initiation, sustained locomotion, and corrective movements. A substantial number of motor cortex neurons (36%) exhibited a sharp increase in firing rate before any overt movement or locomotor-related muscle activity had occurred. Instead, the firing rate of motor cortex neurons significantly decreased during involuntary locomotion compared to quiet standing (p<0.05). Third, we inactivated the left motor cortex with a microinjection of the GABA agonist muscimol. Muscimol immediately suppressed voluntary hindlimb locomotion (p<0.01), despite uncompromised functionality of lumbosacral circuits.

Thus far, functional restoration after SCI has been interpreted as the need to promote long-distance regeneration of severed fibers to their original targets (L. T. Alto et al., Chemotropic guidance facilitates axonal regeneration and synapse formation after spinal cord injury. *Nat Neurosci* 12, 1106 (September, 2009); F. Sun et al., Sustained axon regeneration induced by co-deletion of PTEN and SOCS3. *Nature*, (Nov. 6, 2011)). Undoubtedly, neuroregeneration will be essential following near-complete SCI. However, a more immediate approach might capitalize on the remarkable capacity of spared neuronal systems to reorganize through use-dependent mechanisms (A. Wernig, S. Muller, Laufband locomotion with body weight support improved walking in persons with severe spinal cord injuries. *Paraplegia* 30, 229 (April, 1992); S. Harkema et al., Effect of epidural stimulation of the lumbosacral spinal cord on voluntary movement, standing, and assisted stepping after motor complete paraplegia: a case study. *Lancet* 377, 1938 (Jun. 4, 2011); V. R. Edgerton et al., Training locomotor networks. *Brain Res Rev* 57, 241 (January, 2008)). Here, we established training conditions that not only enabled but also forced the brain to construct a multiplicity of de novo brainstem and intraspinal relays to regain quantitative and qualitative access to electrochemically enabled lumbosacral circuitries. There is growing evidence that active training with appropriate sensory cues is markedly superior to passive, robot-guided rehabilitation to improve stepping capacities in humans ((A. Wernig, S. Muller, Laufband locomotion with body weight support improved walking in persons with severe spinal cord injuries. *Paraplegia* 30, 229 (April, 1992); S. Harkema et al., Effect of epidural stimulation of the lumbosacral spinal cord on voluntary movement, standing, and assisted stepping after motor complete paraplegia: a case study. *Lancet* 377, 1938 (Jun. 4, 2011); V. R. Edgerton et al., Training locomotor networks. *Brain Res Rev* 57, 241 (January, 2008)); L. L. Cai et al., Implications of assist-as-needed robotic step training after a complete spinal cord injury on intrinsic strategies of motor learning. *J Neurosci* 26, 10564 (Oct. 11, 2006); A. Wernig, "Ineffectiveness" of automated locomotor training. *Archives of physical medicine and rehabilitation* 86, 2385 (December, 2005); M. Wirz et al., Effectiveness of automated locomotor training in patients with chronic incomplete spinal cord injury: a multicenter trial. *Archives of physical medicine and rehabilitation* 86, 672 (April, 2005); P. Musienko, R. van den Brand, O. Maerzendorfer, A. Larmagnac, G. Courtine, Combinatory electrical and pharmacological neuroprosthetic interfaces to regain motor function after spinal cord injury. *IEEE Trans Biomed Eng* 56, 2707 (November, 2009)). Likewise, automated treadmill-restricted training, which did not engage cortical neurons, promoted sub-lesional plasticity, but failed to promote remodelling of descending pathways. Treadmill-trained rats did not regain supraspinally-mediated locomotion.

In view of the above description and examples, the present invention introduces a new training paradigm, which encourages active subjects' participation, and triggers a cortex-dependent, activity-based process that restores voluntary control over sophisticated locomotor movements after a SCI leading to chronic paralysis.

These results confirm the capacity of intraspinal circuits to bypass lesions (G. Courtine et al., Recovery of supraspinal control of stepping via indirect propriospinal relay connections after spinal cord injury. *Nature medicine* 14, 69 (January, 2008); F. M. Bareyre et al., The injured spinal cord spontaneously forms a new intraspinal circuit in adult rats. *Nat Neurosci* 7, 269 (March, 2004)), and expand their therapeutic potential to the restoration of function after paralyzing SCI. The ability of training under highly functional states to promote this extensive plasticity and recovery may lead to novel interventions capable of improving function in humans with a range of neuromotor impairments (S. Harkema et al., Effect of epidural stimulation of the lumbosacral spinal cord on voluntary movement, standing, and assisted stepping after motor complete paraplegia: a case study. *Lancet* 377, 1938 (Jun. 4, 2011); B. A. Kakulas, A review of the neuropathology of human spinal cord injury with emphasis on special features. *J Spinal Cord Med* 22, 119 (Summer, 1999); R. Fuentes, P. Petersson, W. B. Siesser, M. G. Caron, M. A. Nicolelis, Spinal cord stimulation restores locomotion in animal models of Parkinson's disease. *Science* 323, 1578 (Mar. 20, 2009)).

The invention claimed is:

1. A method for restoring voluntary control of movement in a subject suffering from a neuromotor disorder comprising:
   a) providing an apparatus for restoring voluntary control of movement in the subject suffering from the neuromotor disorder comprising a multidirectional trunk support system, wherein the multidirectional trunk support system comprises a multidirectional elastic decoupling system, and wherein the multidirectional trunk support system is at least a three dimensional trunk support system;
   b) training said subject by means of the apparatus, wherein training comprises providing postural support against gravity; and
   c) providing neuromodulation to said subject during the training, wherein the neuromodulation comprises electrical stimulation or a combination of electrical stimulation and pharmacological stimulation.

2. The method of claim 1, wherein said electrical stimulation further comprises epidural electrical stimulation.

3. The method of claim 1, wherein said training includes providing said subject with a treadmill exercise.

4. The method of claim 1, wherein the pharmacological stimulation further comprises administering to said subject a pharmaceutical composition comprising a combination of synthetic agonists to monoaminergic receptors, wherein the synthetic agonists are at least two direct agonists of 5HT1A, 5HT2A/C, 5HT7, and DA1-like receptors.

5. The method of claim 4, wherein said pharmaceutical composition further comprises a cocktail of the combination of synthetic agonists to 5HT1A, 5HT2A/C, 5HT7, and DA1-like receptors for use in restoring voluntary control of movement in the subject suffering from the neuromotor disorder and in order to provide an improved balance control which correlates with improved hindlimb locomotion and performance during locomotion.

6. The method of claim 4, wherein restoring voluntary control of movement further comprises restoring voluntary control of limbs.

7. The method of claim 1, wherein said neuromotor disorder is a neuromotor impairment.

8. The method of claim 7, wherein said neuromotor impairment is partial or total paralysis of limbs.

9. The method according to claim 7, wherein said neuromotor impairment is selected from the group consisting of spinal cord injury and consequences of stroke.

* * * * *